（12) United States Patent
Moe et al.

(10) Patent No.: US 8,999,954 B2
(45) Date of Patent: Apr. 7, 2015

(54) INHIBITORS OF POLYSIALIC ACID DE-N-ACETYLASE AND METHODS FOR USING THE SAME

(75) Inventors: Gregory R. Moe, Alameda, CA (US); Brent T. Hagen, Oakland, CA (US)

(73) Assignee: Childern's Hospital & Research Center at Oakland, Oakland, CA (US)

( * ) Notice: Subject to any disclaimer, the term of this patent is extended or adjusted under 35 U.S.C. 154(b) by 638 days.

(21) Appl. No.: 12/167,724

(22) Filed: Jul. 3, 2008

(65) Prior Publication Data

US 2009/0012043 A1    Jan. 8, 2009

Related U.S. Application Data

(60) Provisional application No. 60/958,383, filed on Jul. 3, 2007.

(51) Int. Cl.
  *A61K 31/7008*    (2006.01)
  *A61P 35/00*    (2006.01)
  *A61K 31/70*    (2006.01)

(52) U.S. Cl.
  CPC ............ *A61K 31/70* (2013.01); *A61K 31/7008* (2013.01)

(58) Field of Classification Search
  None
  See application file for complete search history.

(56) References Cited

U.S. PATENT DOCUMENTS

| | | | |
|---|---|---|---|
| 4,021,542 A | 5/1977 | Schmidt et al. | |
| 4,062,950 A | 12/1977 | Frommer et al. | |
| 4,175,123 A | 11/1979 | Junge et al. | |
| 4,216,208 A | 8/1980 | DeBarbieri | |
| 4,254,256 A | 3/1981 | Otani et al. | |
| 4,314,999 A | 2/1982 | DeBarbieri | |
| 4,656,159 A | 4/1987 | Mcpherson et al. | |
| 4,713,374 A | 12/1987 | Della Valle et al. | |
| 4,743,543 A | 5/1988 | Kortright | |
| 4,797,477 A | 1/1989 | Yoshimura et al. | |
| 4,803,303 A | 2/1989 | Horri et al. | |
| 4,840,941 A | 6/1989 | Ueno et al. | |
| 4,914,195 A | 4/1990 | Ogura et al. | |
| 4,968,786 A | 11/1990 | Ogawa et al. | |
| 4,983,725 A | 1/1991 | Miyaji et al. | |
| 5,231,177 A | 7/1993 | Saito et al. | |
| 5,243,035 A | 9/1993 | Nakabayashi et al. | |
| 5,264,424 A | 11/1993 | Della Valle et al. | |
| 5,272,138 A | 12/1993 | Hakomori et al. | |
| 5,332,756 A | 7/1994 | Mongelli et al. | |
| 5,667,285 A | 9/1997 | Seetharaman et al. | |
| 5,674,988 A | 10/1997 | Sabesan | |
| 5,759,823 A | 6/1998 | Wong et al. | |
| 5,962,434 A | 10/1999 | Schnaar et al. | |
| 6,075,134 A | 6/2000 | Bertozzi et al. | |
| 6,110,897 A | 8/2000 | Unverzagt et al. | |
| 6,149,921 A | 11/2000 | Rodriguez et al. | |
| 6,274,568 B1 | 8/2001 | Schnaar et al. | |
| 6,407,072 B1 | 6/2002 | Valle et al. | |
| 6,458,937 B1 | 10/2002 | Bertozzi et al. | |
| 6,548,476 B1 | 4/2003 | Wu et al. | |
| 6,680,054 B1 | 1/2004 | Reece et al. | |
| 6,697,251 B1 | 2/2004 | Aisenberg | |
| 6,936,701 B2 | 8/2005 | Bertozzi et al. | |
| 7,070,801 B2 | 7/2006 | Yamazaki et al. | |
| 7,125,852 B2 * | 10/2006 | Akiyama | 514/23 |
| 7,595,307 B2 | 9/2009 | Moe et al. | |
| 2006/0029621 A1 | 2/2006 | Granoff et al. | |
| 2006/0035267 A1 | 2/2006 | Livingston et al. | |
| 2006/0035284 A1 | 2/2006 | Granoff et al. | |
| 2007/0010482 A1 | 1/2007 | Moe et al. | |
| 2009/0010944 A1 | 1/2009 | Moe et al. | |
| 2009/0010949 A1 | 1/2009 | Moe et al. | |
| 2010/0068728 A1 | 3/2010 | Moe et al. | |
| 2010/0144653 A1 * | 6/2010 | Yarema et al. | 514/25 |
| 2010/0260762 A1 | 10/2010 | Moe et al. | |

FOREIGN PATENT DOCUMENTS

| | | |
|---|---|---|
| WO | WO0109298 | 2/2001 |
| WO | WO0209744 | 2/2002 |
| WO | 03016329 | 2/2003 |
| WO | 03059149 | 7/2003 |
| WO | WO 03/059866 * | 7/2003 |
| WO | WO2007075921 | 1/2006 |
| WO | 2006096663 | 9/2006 |
| WO | WO2006002402 | 7/2007 |
| WO | WO2009047792 | 4/2009 |

OTHER PUBLICATIONS

Biological properties of N-acyl and N-haloacetyl neuraminic acids . . . Bioorg. Med. Chem. (2002) vol. 10, pp. 3175-3185.*
Yamamoto, K. "N-acyl specificity of Taka-N-acetyl-beta-D-glucosaminidase . . . " J. Biochem. (1973) vo 73, pp. 749-753.*
Angelino, N. et al "Versatile intermediates in the selective modification of the amino function . . . " Carbohyd. Res. (1995) vol. 276, pp. 99-115.*
Vavasseur, F. et al "Synthesis of O-glycan core 3 . . . " Glycobiology (1995) vol. 5, No. 3, pp. 351-357.*
Wartchow, C. et al "Carbohydrate protease conjugates . . . " J. Org. Chem. (1995) vol. 60, pp. 2216-2226.*

(Continued)

*Primary Examiner* — Layla Bland
(74) *Attorney, Agent, or Firm* — Rudy J. Ng; Carol L. Francis; Bozicevic, Field & Francis LLP

(57) ABSTRACT

The invention relates to inhibitors of polysialic (PSA) de-N-acetylase, methods of their production and use. The methods involve use of a PSA de-N-acetylase inhibitor for modifying the growth of cells, such as inhibiting the growth of cancer cells. The compositions include an inhibitor of a PSA de-N-acetylase, such as N-substituted derivatives of the amino sugars hexosamine and neuraminic acid, as well as conjugates and aggregates. Also provided are pharmaceutical compositions that include a PSA de-N-acetylase inhibitor of the invention. Kits containing one or more inhibitor compositions of the invention, as well as methods of preparing the compositions also are provided.

15 Claims, 7 Drawing Sheets

(56) References Cited

OTHER PUBLICATIONS

Behling, U. et al "Synthetic glycolipid adjuvants" J. Immunol. (1976) vol. 117, No. 3, pp. 847-851.*
Vippagunta, S. et al "Crystalline solids" Adv. Drug Deliv. (2001) vol. 48, pp. 3-26.*
Pon et al. Glycobiology vol. 17, No. 3, pp. 249-260, Dec. 15, 2006.*
Zou et al. The Journal of Biological Chemistry, vol. 279, No. 24, Issue of Jun. 11, pp. 25390-25399, 2004.*
Ashcroft et al. Biochem. J. (1976) 154, 701-707.*
Garcia-Martin et al. Polymer 41 (2000) 821-826.*
Thomas, Journal of Medicinal Chemistry, 1970, vol. 13, No. 4, pp. 755-756.*
Fondy, et al., Haloacetamido analogs of 2-amino-2-deoxy-D-mannose. Syntheses and effects on tumor-bearing mice., J. Med. Chem., 1981, 24 (7), pp. 848-852.
Angata, et al. Chem.,Chemical diversity in the sialic acids and related a-keto acids: an evolution perspective,Rev. 2002, 102:439-469, No. 2.
Bardor, et al.,Mechanism of uptake and incorporation of the non-human sialic acid n-glycolyneuraminic acid into human cells, Biol. Chem. 2005, 280:4228-4237, No. 6.
Chamas, et al., De-N-acetyl-gangliosides in humans: unusual subcellular distribution of a novel tumor antigen, Cancer res. 1999, 59:1337-1346.
Collins, et al.,Conversion of cellular sialic acid expression from N-acetyl-to-N-glycolylneuraminic acid using a synthetic precursor . . . ,Glycobiology 2000, 10:11-20, No. 1.
Dall'Olio, Protein glycosylation in cancer biology:an overview, clin. Pathol: Mol. Panthol. 1996, 49:M126-M135.
Hakamori, Tumor malignancy defined by aberrant glycosylation and sphingo(glyco)lipid metabolism, Cancer res, 1996, 56:5309-5318.
Hanai, et al., A novel ganglioside, de-N-acetyl-GM3 (II3NeuNH2LacCer), acting as a strong promoter for epidermal growth factor . . . , J. Biol. Chem., 1988, 263:6296-6301, No. 13.
Kayser, et al., Biosynthesis of a nonphyssiological sialic acid in different rat organs, using N-propanoyl-d-hexosamines . . . , J.Biol. Chem. 1992, 267:16934-16938, No. 24.
Keppler, et al., Biochemical engineering of the N-acyl side chain of sialic acid:biological implications, Glycobiology, 2001, 11:11R-18R, No. 2.
Kim, et al., Perspectives on the significance of altered glycosylation of glycoproteins in cancer, Glycoconjugate journ. 1997, 14:569-576.
Luchansky, et al., Constructing azide-labeled cell surfaces using polysaccharide biosynthetic pathways, Meth. Enzymol. 2003, 362:249-272.
Manzi, et al., Biosynthesis and turnover of O-acetyl and N-acetyl groups in the gangliosides of human melanoma cells, J. Biol. Chem. 1990, 265:13091-13103, No. 22.
Oetke, et al., Evidence for efficient uptake and incorporation of sialic acid by eukaryotic cells, Eur. J. Biochem, 2001, 268:4553-4561.
Popa, et al., Purification and structural characterization of de-N-acetylated form of GDE ganglioside present in human melanoma tumors, Glycobiology, 2007, 17:367-373, No. 4.
Sjoberg, et al., Expression of De-N-acetyl-gangliosides in human melanoma cells is induced by genistein or nocodazole, J. Biol. Chem, 1995, 270:2921-2930, No. 7.
Chiou, et al., 1971, "Pharmaceutical Applications of Solid Dispersion Systems", J. Pharma Sci., 60(9):1281-1302.
Singh, et al., 2004, "Adsorption behavior of selected monosaccharides onto an alumina interface", J Colloid Interface Sci., 270(1):21-28.
Ogihara, et al., 2002, Continuous Synthesis of Monodispersed Alumina Particles by the Hydrolysis of Metal Alkoxide Using a Taylor Vortex, Kona, 20:231-237.
Wen, et al., 2000, "Growth characteristics of boehmite-derived ultrane theta and alpha-alumina particles during phase transformation", J. Crystal Growth, 208:696-708.
Windhab, E.J., 2000, "Fluid Immobilization—A Structure-Related Key Mechanism for the Viscous Flow Behavior of Concentrated Suspension Systems" Appl. Rheol, 10(3):134-144.
Pusino, et al., 1989, "D-Glucosamine Sorption on Cu(II)-Montmorillonite as the Protonated and Neutral Species", Clays and Clay Minerals, 37(4):377-380.
Livingston et al. (1988) "Extended Polysialic Acid Chains (n > 55) in Glycoproteins from Human Neuroblastoma Cells" J Biol Chem 265(19):9443-9448.
Raevilla-Nuin et al. (2002) "Transport of N-Acetyl-Mannosamine and N-Acetyl-Glucosamine in *Escherichia coli* K1: Effect on Caspular Polysialic Acid Production" FEBS Lett 511(1-3):97-101.

* cited by examiner

INHIBITORS OF POLYSIALIC ACID DE-N-ACETYLASE AND METHODS FOR USING THE SAME

CROSS-REFERENCE TO RELATED APPLICATION

This application claims priority benefit of U.S. provisional application Ser. No. 60/958,383, filed Jul. 3, 2007, which application is incorporated herein by reference in its entirety.

STATEMENT REGARDING FEDERALLY SPONSORED RESEARCH

This invention was made with government support under grants no. AI64314 awarded by the National Institute of Allergy and Infectious Diseases, and the National Institute of Health. The government has certain rights in this invention.

TECHNICAL FIELD

This disclosure relates to inhibitors of polysialic acid de-N-acetylase, compositions containing the same, methods of their manufacture and use.

BACKGROUND

Sialic acid is an N- or O-substituted derivative of neuraminic acid. The N-substituted versions generally bear either an acetyl or a glycolyl group. In contrast, the O-substituted hydroxyl group may vary considerably, e.g., acetyl, lactyl, methyl, sulfate and phosphate groups. Polysialic acids are also quite common in which N-acetyl neuraminic acid residues are linked via the C2 ketal OH to another molecule by a glycosidic bond, e.g., poly alpha (2→8) N-acetyl neuraminic acid.

The sialic acids are biologically important carbohydrates found in organisms ranging from bacteria to humans. They are common features decorating the terminal ends of glycoproteins, glycans and glycosphingolipids, as well as other molecules. They mediate myriad normal cellular activities. This includes stabilizing glycoconjugates in cell membranes, regulating cell-cell interactions, acting as chemical messengers, regulating transmembrane receptor function, affecting membrane transport, controlling the half-lives of circulating glycoproteins and cells, and contributing to the permselectivity of the glomerular endothelium. See for review: Angata and Varki Chem. Rev. (2002) 102:439.

Given their prominent role in normal cellular activity, sialic acid and its derivatives have been used as markers for abnormal cellular processes such as cancer. (O'Kennedy et al., Cancer Lett., 1991 58:91; Vedralova et al. Cancer Lett. 1994 78:171; and Horgan et al., Clin. Chim. Acta., 1982 118:327; and Narayanan, S. Ann. Clin. Lab. Sci. 1994 24:376). For instance, cancer cells that can metastasize often have larger amounts of sialic acid-modified glycoproteins, which may help them enter the blood stream. Also, it has long been recognized that the sialic acid of tumor cells is modified in ways that differ from normal cells (Hakamori Cancer Res. 1996, 56:5309, Dall'Olio Clin. Mol. Pathol. 1996, 49:M126, Kim and Varki Glycoconj. J. 1997, 14:569).

One sialic acid derivative thought to be uncommon in normal cells, but present on cancer cells is de-N-acetyl sialic acid (Hanai et al J. Biol. Chem. 1988, 263:6296, Manzi et al J. Biol. Chem. 1990, 265:1309, Sjoberg et al J. Biol. Chem. 1995, 270:2921, Chamas et al 1999, Cancer Res. 59:1337; and Popa et al Glycobiology. 2007 17:367).

The aminohydrolase superfamily includes deacetylase enzymes that specifically remove ("deacetylate") the N-acyl groups from amino sugars. These enzymes are called de-N-acetylases. For instance, the ganglioside de-N-acetyl GD3 is present in human melanoma tumors, and the fatty acid content suggests the existence of a de-N-acetylase mostly active on the molecular species of gangliosides with short-chain fatty acids (Popa et al. (2007) Glycobiology 17(4):367). The enzyme N-acetyl-D-glucosaminyl-phosphatidylinositol de-N-acetylase (Glc-NAc-PI de-N-acetylase) is found in various organisms including humans (Watanabe et al. Biochem. J. (1999) 339:185; and Urabiak et al. (2005) J. Biol. Chem. 280(24):22831). This enzyme is involved in catalytic removal of the acetyl group from the N-amino of Glc-NAc-PI and release of acetate to generate the de-acetylated form of the amino sugar (Guther et al. (2006) Mol Biol Cell. 17(12): 5265).

Literature

Amino sugars, derivatives and related literature of interest are reported in the following U.S. Pat. Nos. 4,021,542; 4,062,950; 4,175,123; 4,216,208; 4,254,256; 4,314,999; 4,656,159; 4,713,374; 4,797,477; 4,803,303; 4,840,941; 4,914,195; 4,968,786; 4,983,725; 5,231,177; 5,243,035; 5,264,424; 5,272,138; 5,332,756; 5,667,285; 5,674,988; 5,759,823; 5,962,434; 6,075,134; 6,110,897; 6,274,568; 6,407,072; 6,458,937; 6,548,476; 6,697,251; 6,680,054; 6,936,701; and 7,070,801, and in the following references: Angata and Varki Chem. Rev. 2002, 102:439; Hakamori Cancer Res. 1996, 56:5309; Dall'Olio Clin. Mol. Pathol. 1996, 49:M126; Kim and Varki Glycoconj. J. 1997, 14:569; Hanai et al J. Biol. Chem. 1988, 263:6296; Manzi et al J. Biol. Chem. 1990, 265:1309; Sjoberg et al J. Biol. Chem. 1995, 270:2921; Chamas et al Cancer Res. 1999, 59:1337; Popa et al Glycobiology. 2007 17:367; Kayser et al J. Biol. Chem. 1992 267: 16934; Keppler et al Glycobiology 2001, 11:11R; Luchansky et al Meth. Enzymol. 2003, 362:249; Oetke et al Eur. J. Biochem. 2001, 268:4553; Collins et al Glycobiology 2000, 10:11; and Bardor et al J. Biol. Chem. 2005, 280:4228. See also US 2007/0010482; U.S. application Ser. No. 11/645,255, filed Dec. 22, 2006; WO 2006/002402; and PCT application serial no. PCT/US2006/04885, filed Dec. 22, 2006.

SUMMARY OF THE INVENTION

The invention relates to compositions for inhibiting polysialic acid (PSA) de-N-acetylase, and methods of their production and use. The methods of the invention involve use of an inhibitor of PSA de-N-acetylase for modifying the growth of cells, such as inhibiting the growth of cancer cells by administering an effective amount of the inhibitor to facilitate reduction in viability of the cancerous cells exposed to the inhibitor. The compositions of the invention generally comprise an inhibitor of a PSA de-N-acetylase, and include N-substituted derivatives of the amino sugars hexosamine and neuraminic acid, as well as conjugates and aggregates. Also provided are pharmaceutical compositions that include an effective amount of an inhibitor of a PSA de-N-acetylase in a pharmaceutically acceptable vehicle. The invention also provides kits containing one or more compositions of the invention, as well as methods of preparing the compositions.

In certain embodiments, the method of production of PSA de-N-acetylase inhibitors, and methods of production of polysialic acid conjugates, involves production of an aggregate comprising a polysialic acid de-N-acetylase inhibitor or a polysialic acid conjugate comprising admixing monomers of one or more polysialic acid de-N-acetylase inhibitors under aggregating conditions so as to form and aggregate. In exemplary embodiments, the aggregating conditions is heating (e.g., heating to 30° C. to 70° C.) or the addition of an aggregating excipient (e.g., aluminum hydroxide). Such methods can provide for production of an aggregate that is a particle, which particle can be a microscopic particle.

Accordingly, in one aspect, the present disclosure features methods of inhibiting growth of a cancerous cell in a subject, said method comprising administering to the subject an effective amount of a pharmaceutically acceptable formulation comprising an inhibitor of a polysialic acid (PSA) de-N-acetylase, wherein the inhibitor is an N-substituted derivative of an amino sugar selected from the group consisting of a hexosamine compound of formula (I), and a neuraminic acid compound of formula (II):

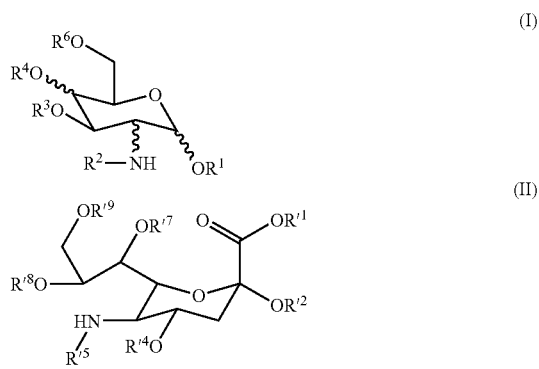

or the pharmaceutically acceptable salts, solvate, hydrates, prodrug, anomers, tautomers and stereoisomers forms thereof;

wherein —NH—$R^2$ and —NH—$R'^5$ comprise an inhibitor of an amide bond hydrolysis reaction catalyzed by said PSA de-N-acetylase;

each $R^1$, $R'^1$, $R'^2$, $R^3$, $R^4$, $R'^4$, $R^6$, $R'^7$, $R'^8$ and $R'^9$ is independently hydrogen or a substituted or unsubstituted moiety selected from the group consisting of heteroatom, alkyl, aryl, cycloalkyl, heteroaryl, alkenyl, acyl, sulfonyl, carbohydrate, lipid, nucleic acid, peptide, dye, fluorophore and polypeptide, with the proviso that said inhibitor of PSA de-N-acetylase is other than an unacetylated or tetra-O-acetylated N-fluoroacetyl mannosamine; an unacetylated or tetra-O-acetylated N-fluoroacetyl galactosamine; an unacetylated or tetra-O-acetylated N-fluoroacetyl glucosamine; an unacetylated or tetra-O-acetylated N-chloroacetyl mannosamine; an unacetylated or tetra-O-acetylated N-chloroacetyl galactosamine; an unacetylated or tetra-O-acetylated N-chloroacetyl glucosamine; an unacetylated or tetra-O-acetylated N-bromoacetyl mannosamine; an unacetylated or tetra-O-acetylated N-bromoacetyl galactosamine; and an unacetylated or tetra-O-acetylated N-bromoacetyl glucosamine; and wherein said administering facilitates reduction in viability of cancerous cells exposed to said inhibitor.

In related embodiments the cancerous cells comprise a de-N-acetylated sialic acid (deNAc SA) epitope. In further related embodiments the subject comprises the deNAc SA epitope on a surface of the cancerous cell during cell division. In exemplary embodiments the cancer is a melanoma, a leukemia, or a neuroblastoma. In related embodiments, the inhibitor is administered by infusion or by local injection, and can be administered prior to surgical intervention to remove cancerous cells or at the time of or after surgical intervention to remove cancerous cells. In further related embodiments, the inhibitors are administered in conjunction with at least one of an immunotherapy, a cancer chemotherapy or a radiation therapy to the subject.

In further related embodiments, the N-substituted derivative of an amino sugar comprises a conjugate of two or more molecules. In related embodiments, the conjugate can modify cellular uptake relative to unconjugated substrate inhibitor. In related embodiments, $R^2$ and $R'^5$ of the compound are selected from the group consisting of haloacetyl, acyl and sulfonyl. In related embodiments, the haloacetyl is a radical selected from the group consisting of —C(O)CH$_2$F, —C(O)CH$_2$Cl, —C(O)CH$_2$Br, —C(O)CH$_2$I, —C(O)CHF$_2$, —C(O)CHCl$_2$, —C(O)CHBr$_2$, —C(O)CF$_3$, —C(O)CCl$_3$, and —C(O)CBr$_3$; the acyl is a radical selected from the group consisting of —C(O)CH=CH$_2$ and —C(O)C(=CH$_2$)(CH$_3$); and the sulfonyl is a radical selected from the group consisting of —S(=O)$_2$(CH$_3$).

In further related embodiments, the hexosamine compound of formula (I) is selected from a mannosamine compound of formula (III), a galactosamine compound of formula (IV), or a glucosamine compound of formula (V):

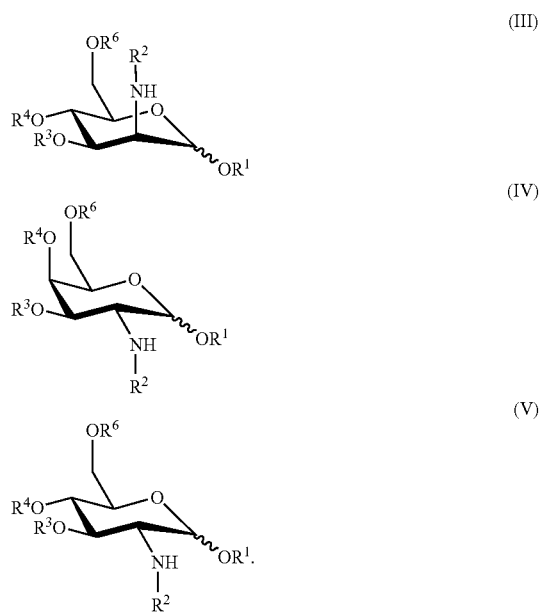

In related embodiments, each $R^1$, $R^3$, $R^4$ and $R^6$ of the above formulae is independently selected from the group consisting of hydrogen and substituted or unsubstituted acyl, and each $R^2$ is independently selected from a radical of the group consisting of —C(O)CH=CH$_2$, —C(O)C(=CH$_2$)(CH$_3$), —C(O)CH$_2$F, —C(O)CH$_2$Cl, —C(O)CH$_2$Br, —C(O)CH$_2$I, —S(=O)$_2$(CH$_3$), —C(O)CHF$_2$, —C(O)CHCl$_2$, —C(O)CHBr$_2$, —C(O)CF$_3$, —C(O)CCl$_3$, and —C(O)CBr$_3$.

In specific embodiments the inhibitor comprises an N-substituted hexosamine selected from the group consisting of: N-acryl mannosamine; N-acryl galactosamine; N-acryl glucosamine; N-methacryl mannosamine; N-methacryl galactosamine; N-methacryl glucosamine; N-iodoacetyl mannosamine; N-iodoacetyl galactosamine; N-iodoacetyl glucosamine; N-methanesulfonyl mannosamine; N-methanesulfonyl galactosamine; N-methanesulfonyl glucosamine; N-difluoroacetyl mannosamine; N-difluoroacetyl galactosamine; N-difluoroacetyl glucosamine; N-dichloroacetyl mannosamine; N-dichloroacetyl galactosamine;

N-dichloroacetyl glucosamine; N-dibromoacetyl mannosamine; N-dibromoacetyl galactosamine; N-dibromoacetyl glucosamine; N-trifluoroacetyl mannosamine; N-trifluoroacetyl galactosamine; N-trifluoroacetyl glucosamine; N-trichloroacetyl mannosamine; N-trichloroacetyl galactosamine; N-trichloroacetyl glucosamine; N-tribromoacetyl mannosamine; N-tribromoacetyl galactosamine; and N-tribromoacetyl glucosamine; or the pharmaceutically acceptable salts, solvate, hydrates, and prodrug forms thereof, anomers, tautomers and stereoisomers thereof, and derivatives thereof.

In further specific embodiments, the inhibitor comprises an N-substituted neuraminic acid selected from the group consisting of: N-acryl neuraminic acid; N-methacryl neuraminic acid; N-fluoroacetyl neuraminic acid; N-chloroacetyl neuraminic acid; N-bromoacetyl neuraminic acid; N-iodoacetyl neuraminic acid; N-methyanesulfonyl neuraminic acid; N-difluoroacetyl neuraminic acid; N-dichloroacetyl neuraminic acid; N-dibromoacetyl neuraminic acid; N-trifluoroacetyl neuraminic acid; N-trichloroacetyl neuraminic acid; and N-tribromoacetyl neuraminic acid; or the pharmaceutically acceptable salts, solvate, hydrates, and prodrug forms thereof, anomers, tautomers and stereoisomers thereof, and derivatives thereof.

In related embodiments, the inhibitor comprises an aggregate, which may comprise a microscopic particle.

In another aspect, the present disclosure provides pharmaceutical compositions comprising an effective amount of an inhibitor of a polysialic acid (PSA) de-N-acetylase in a pharmaceutically acceptable vehicle, wherein said inhibitor is an N-substituted derivative of a hexosamine compound of formula (I), or an N-substituted derivative of an neuraminic acid compound of formula (II):

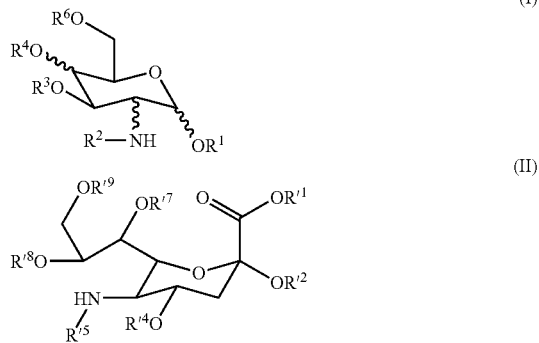

or the pharmaceutically acceptable salts, solvate, hydrates, and prodrug forms thereof, anomers, tautomers and stereoisomers thereof;

wherein $R^2$ and $R'^5$ are selected from the group consisting of haloacetyl, acylalkenyl, and sulfonyl; and each $R^1$, $R'^1$, $R'^2$, $R^3$, $R^4$, $R'^4$, $R^6$, $R'^7$, $R'^8$ and $R'^9$ is independently hydrogen or a substituted or unsubstituted moiety selected from the group consisting of heteroatom, alkyl, aryl, cycloalkyl, heteroaryl, alkenyl, acyl, sulfonyl, carbohydrate, lipid, nucleic acid, peptide, dye, fluorophore and polypeptide, with the proviso that said inhibitor of PSA de-N-acetylase is other than an unacetylated or tetra-O-acetylated N-fluoroacetyl mannosamine; an unacetylated or tetra-O-acetylated N-fluoroacetyl galactosamine; an unacetylated or tetra-O-acetylated N-fluoroacetyl glucosamine; an unacetylated or tetra-O-acetylated N-chloroacetyl mannosamine; an unacetylated or tetra-O-acetylated N-chloroacetyl galactosamine; an unacetylated or tetra-O-acetylated N-chloroacetyl glucosamine; an unacetylated or tetra-O-acetylated N-bromoacetyl mannosamine; an unacetylated or tetra-O-acetylated N-bromoacetyl galactosamine; and an unacetylated or tetra-O-acetylated N-bromoacetyl glucosamine.

In related embodiments, the haloacetyl of the inhibitor compound is a radical selected from the group consisting of —C(O)CH$_2$F, —C(O)CH$_2$Cl, —C(O)CH$_2$Br, —C(O)CH$_2$I, —C(O)CHF$_2$, —C(O)CHCl$_2$, —C(O)CHBr$_2$, —C(O)CF$_3$, —C(O)CCl$_3$, and —C(O)CBr$_3$; the acylalkenyl is a radical selected from the group consisting of —C(O)CH=CH$_2$ and —C(O)C(=CH$_2$)(CH$_3$); and the sulfonyl is a radical selected from the group consisting of —S(=O)$_2$(CH$_3$).

In further related embodiments, the hexosamine compound of formula (I) is selected from a mannosamine compound of formula (III), a galactosamine compound of formula (IV), or a glucosamine compound of formula (V):

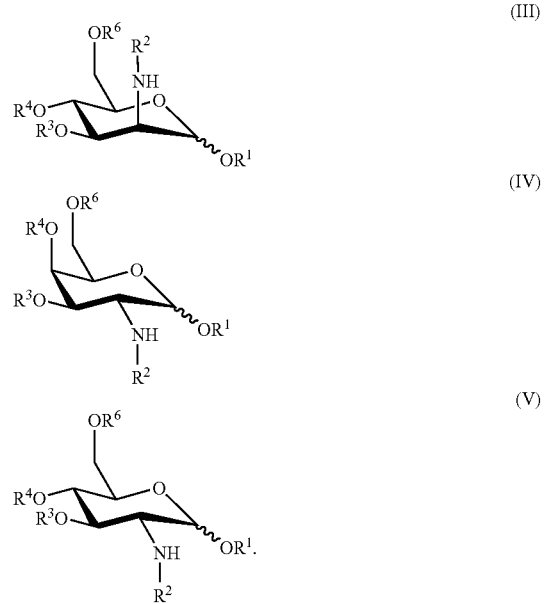

In further embodiments, each $R^1$, $R^3$, $R^4$ and $R^6$ of the above formulae is independently selected from the group consisting of hydrogen and substituted or unsubstituted acyl, and each $R^2$ is independently selected from a radical of the group consisting of —C(O)CH=CH$_2$, —C(O)C(=CH$_2$)(CH$_3$), —C(O)CH$_2$F, —C(O)CH$_2$Cl, —C(O)CH$_2$Br, —C(O)CH$_2$I, —S(=O)$_2$(CH$_3$), —C(O)CHF$_2$, —C(O)CHCl$_2$, —C(O)CHBr$_2$, —C(O)CF$_3$, —C(O)CCl$_3$, and —C(O)CBr$_3$.

In further related embodiments, the inhibitor of the pharmaceutical composition can comprise an aggregate, which can comprise a microscopic particle.

In another aspect, the disclosure provides pharmaceutical compositions comprising an effective amount of an inhibitor of a polysialic acid (PSA) de-N-acetylase in a pharmaceutically acceptable vehicle, wherein said inhibitor comprises an N-substituted hexosamine selected from the group consisting of: N-acryl mannosamine; N-acryl galactosamine; N-acryl glucosamine; N-methacryl mannosamine; N-methacryl galactosamine; N-methacryl glucosamine; N-iodoacetyl mannosamine; N-iodoacetyl galactosamine; N-iodoacetyl glucosamine; N-methyanesulfonyl mannosamine; N-methyanesulfonyl galactosamine; N-methyanesulfonyl glucosamine; N-difluoroacetyl mannosamine; N-difluoroacetyl galactosamine; N-difluoroacetyl glucosamine; N-dichloroacetyl mannosamine; N-dichloroacetyl galactosamine; N-dichloroacetyl glucosamine; N-dibromoacetyl mannosamine; N-dibromoacetyl galactosamine; N-dibromoacetyl glucosamine; N-trifluoroacetyl mannosamine; N-trifluoroacetyl galactosamine; N-trifluoroacetyl glucosamine; N-trichloroacetyl mannosamine; N-trichloroacetyl galactosamine; N-trichloroacetyl glucosamine; N-tribromoacetyl mannosamine; N-tribromoacetyl galactosamine; and N-tribromoacetyl glucosamine; or the pharmaceutically acceptable salts, solvate, hydrates, and prodrug forms thereof, anomers, tautomers and stereoisomers thereof, and derivatives thereof. The inhibitor of such pharmaceutical composition can comprise an aggregate, which can comprise a microscopic particle.

In another aspect, the present disclosure provides pharmaceutical compositions comprising an effective amount of an inhibitor of a polysialic acid (PSA) de-N-acetylase in a pharmaceutically acceptable vehicle, wherein said inhibitor comprises an N-substituted neuraminic acid selected from the group consisting of: N-acryl neuraminic acid; N-methacryl neuraminic acid; N-fluoroacetyl neuraminic acid; N-chloroacetyl neuraminic acid; N-bromoacetyl neuraminic acid; N-iodoacetyl neuraminic acid; N-methyanesulfonyl neuraminic acid; N-difluoroacetyl neuraminic acid; N-dichloroacetyl neuraminic acid; N-dibromoacetyl neuraminic acid; N-trifluoroacetyl neuraminic acid; N-trichloroacetyl neuraminic acid; and N-tribromoacetyl neuraminic acid; or the pharmaceutically acceptable salts, solvate, hydrates, and prodrug forms thereof, anomers, tautomers and stereoisomers thereof, and derivatives thereof. The inhibitor of such pharmaceutical composition can comprise an aggregate, which can comprise a microscopic particle.

In a further aspect, the present disclosure provides compositions comprising an N-substituted hexosamine selected from the group consisting of: N-acryl mannosamine; N-acryl galactosamine; N-acryl glucosamine; N-methacryl mannosamine; N-methacryl galactosamine; N-methacryl glucosamine; N-iodoacetyl mannosamine; N-iodoacetyl galactosamine; N-iodoacetyl glucosamine; N-methyanesulfonyl mannosamine; N-methyanesulfonyl galactosamine; N-methyanesulfonyl glucosamine; N-difluoroacetyl mannosamine; N-difluoroacetyl galactosamine; N-difluoroacetyl glucosamine; N-dichloroacetyl mannosamine; N-dichloroacetyl galactosamine; N-dichloroacetyl glucosamine; N-dibromoacetyl mannosamine; N-dibromoacetyl galactosamine; N-dibromoacetyl glucosamine; N-trifluoroacetyl mannosamine; N-trifluoroacetyl galactosamine; N-trifluoroacetyl glucosamine; N-trichloroacetyl mannosamine; N-trichloroacetyl galactosamine; N-trichloroacetyl glucosamine; N-tribromoacetyl mannosamine; N-tribromoacetyl galactosamine; and N-tribromoacetyl glucosamine; or the pharmaceutically acceptable salts, solvate, hydrates, and prodrug forms thereof, anomers, tautomers and stereoisomers thereof, and derivatives thereof. The inhibitor of such compositions can comprise an aggregate, which can comprise a microscopic particle.

In a further aspect, the present disclosure provides compositions comprising an N-substituted neuraminic acid selected from the group consisting of: N-acryl neuraminic acid; N-methacryl neuraminic acid; N-fluoroacetyl neuraminic acid; N-chloroacetyl neuraminic acid; N-bromoacetyl neuraminic acid; N-iodoacetyl neuraminic acid; N-methyanesulfonyl neuraminic acid; N-difluoroacetyl neuraminic acid; N-dichloroacetyl neuraminic acid; N-dibromoacetyl neuraminic acid; N-trifluoroacetyl neuraminic acid; N-trichloroacetyl neuraminic acid; and N-tribromoacetyl neuraminic acid; or the pharmaceutically acceptable salts, solvate, hydrates, and prodrug forms thereof, anomers, tautomers and stereoisomers thereof, and derivatives thereof. The inhibitor of such compositions can comprise an aggregate, which can comprise a microscopic particle.

In another aspect, the present disclosure provides kits which find use in treating a host suffering from a cellular proliferative disease condition, said kit comprising an inhibitor of polysialic acid (PSA) de-N-acetylase as disclosed herein and instructions for the effective use of said inhibitor in a method of inhibiting the growth of a cancerous cell. In related embodiments, the kit further includes a diagnostic for detecting a de-N-acetylated sialic acid (deNAc SA) epitope, which diagnostic can comprise an antibody or derivative thereof suitable for detecting a de-N-acetylated sialic acid (deNAc SA) epitope on an extracellularly accessible surface of a cancer cell (e.g., a SEAM 3 antibody (ATCC Deposit No. HB-12170). In related embodiments, the N-substituted derivative of an amino sugar of the kit comprises a conjugate of two or more molecules, where the conjugate can, for example, modify cellular uptake relative to unconjugated substrate inhibitor, and/or can comprise a detectable label (e.g., a fluorophore). The inhibitor of the kits disclosed herein can be provided in a composition in which the inhibitors comprises an aggregate, which aggregates can comprise a microscopic particle.

In other aspects, the present disclosure provides methods of producing an aggregate comprising a polysialic acid de-N-acetylase inhibitor or a polysialic acid conjugate, the method comprising admixing monomers of one or more polysialic acid de-N-acetylase inhibitors under aggregating conditions so as to form an aggregate. In related embodiments, the aggregating condition is heating or the addition of an aggregating excipient (e.g., heating from 30° C. to 70° C.). In related embodiments, the aggregating excipient is aluminum hydroxide. In further related embodiments, the aggregate is a particle, e.g., a microscopic particle.

Other features of the invention are described herein, and will also be readily apparent to the ordinarily skilled artisan upon reading the present disclosure.

DETAILED DESCRIPTION OF EXEMPLARY EMBODIMENTS

Figure 1:
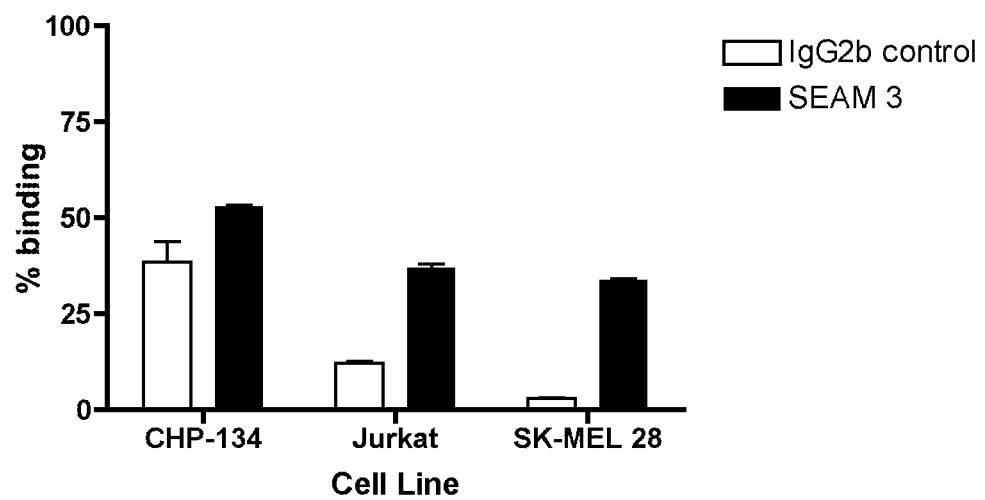
FIG. 1 is a graph summarizing the binding of a monoclonal antibody, SEAM 3, that recognizes neuraminic acid-containing PSA. The error bars represent the standard deviation of three replicate determinations.

The present invention is based in part on the discovery that growth and viability of cancer cells expressing antigens of polysialic acid ("PSA") containing one or more neuraminic acid residues (i.e., a deNAc SA epitope) can be modified or otherwise arrested by administration of an inhibitor of the enzyme polysialic acid de-N-acetylase ("PSA de-N-acetylase"). Inhibitory compounds include derivatives of various modified substrates or compounds that otherwise bind and inhibit the enzyme, such as N-substituted derivatives of hexosamine and neuraminic acid. Additional inhibitor compounds are conjugates of the N-substituted hexosamine and neuraminic acid derivatives, such as a conjugate of an N-substituted hexosamine and a peptide, polypeptide, nucleic acid, dye, lipid or carbohydrate for adapting the characteristics of the inhibitor for a particular given end use.

Before the present invention and specific exemplary embodiments of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an inhibitor" includes a plurality of such antigens and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. To the extent a definition of a term set out in a document incorporated herein by reference conflicts with the definition of a term explicitly defined herein, the definition set out herein controls.

Definitions

When describing the compounds, pharmaceutical compositions containing such compounds and methods of using such compounds and compositions, the following terms have the following meanings unless otherwise indicated. It should also be understood that any of the moieties defined forth below may be substituted with a variety of substituents, and that the respective definitions are intended to include such substituted moieties within their scope.

"Acyl" refers to a radical —C(O)R, where R is hydrogen, alkyl, cycloalkyl, heterocycloalkyl, aryl, arylalkyl, heteroalkyl, or heteroaryl as defined herein. Representative examples include, but are not limited to, formyl, acetyl, cyclohexylcarbonyl, cyclohexylmethylcarbonyl, benzoyl, benzylcarbonyl and the like.

"Acylamino" refers to a radical —NR'C(O)R, where R' is hydrogen, alkyl, cycloalkyl, heterocycloalkyl, aryl, arylalkyl, heteroalkyl, heteroaryl, heteroarylalkyl and R is hydrogen, alkyl, alkoxy, cycloalkyl, heterocycloalkyl, aryl, arylalkyl, heteroalkyl, heteroaryl or heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Acyloxy" refers to the group —OC(O)H, —OC(O)-alkyl, —OC(O)-aryl or —OC(O)-cycloalkyl.

"Aliphatic" refers to hydrocarbyl organic compounds or groups characterized by a straight, branched or cyclic arrangement of the constituent carbon atoms and an absence of aromatic unsaturation. Aliphatics include, without limitation, alkyl, alkylene, alkenyl, alkynyl and alkynylene. Aliphatic groups typically have from 1 or 2 to 6 or 12 carbon atoms.

"Alkenyl" refers to monovalent olefinically unsaturated hydrocarbyl groups having up to about 11 carbon atoms, particularly, from 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH=CH$_2$), n-propenyl (—CH$_2$CH=CH$_2$), isopropenyl (—C(CH$_3$)=CH$_2$), vinyl and substituted vinyl, and the like.

"Alkoxy" refers to the group —O-alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like. A "lower alkoxy" group intends an alkoxy group containing from 1 to 6, or from 1 to 4, carbon atoms. Likewise, the terms "alkenoxy" and "alkynoxy" as used herein intend an alkenyl or alkynyl group bound through a single, terminal ether linkage, that is, an "alkenoxy" or "alkynoxy" group may be (defined as —OR where R is alkenyl or alkynyl).

"Alkoxycarbonyl" refers to a radical —C(O)-alkoxy where alkoxy is as defined herein.

"Alkoxycarbonylamino" refers to the group —NRC(O)OR' where R is hydrogen, alkyl, aryl or cycloalkyl, and R' is alkyl or cycloalkyl.

"Alkyl" refers to monovalent saturated aliphatic hydrocarbyl groups particularly having 1 to 24 carbon atoms, more particularly as a lower alkyl, from 1 to 8 carbon atoms and still more particularly, from 1 to 6 carbon atoms, or even 1 to 4 carbons. The hydrocarbon chain may be either straight-chained or branched. This term is exemplified by groups such as methyl, ethyl, n-propyl, isopropyl, n-butyl, iso-butyl, tert-butyl, n-hexyl, n-octyl, tert-octyl and the like. The term "alkyl" also includes "cycloalkyls."

"Alkylene" refers to divalent saturated aliphatic hydrocarbyl groups particularly having up to about 12 or 18 carbon atoms and more particularly 1 to 6 carbon atoms which can be straight-chained or branched. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

"Alkenyl" refers to a mono-unsaturated or poly-unsaturated hydrocarbon group 2 to 24 carbon atoms. Groups contemplated within this class contain 2 to 12 carbon atoms likewise, the term "alkynyl" as used herein intends a hydrocarbon group of 2 to 24 carbon atoms containing at least one triple bond. Groups within this class contain 2 to 12 carbon atoms. Other groups contain 2 to 4 carbon atoms, 2 to 3 carbon atoms, and 2 carbon atoms.

"Alkynyl" refers to acetylenically unsaturated hydrocarbyl groups particularly having up to about 12 or 18 carbon atoms and more particularly 2 to 6 carbon atoms which can be straight-chained or branched and having at least 1 and particularly from 1 to 2 sites of alkynyl unsaturation. Particular non-limiting examples of alkynyl groups include acetylenic, ethynyl (—C≡CH), propargyl (—CH$_2$C≡CH), and the like.

"Amino" refers to the radical —NH$_2$.

"Amino acid" refers to any of the naturally occurring amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D, L, or DL form. The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine).

"Aminocarbonyl" refers to the group —C(O)NRR where each R is independently hydrogen, alkyl, aryl or cycloalkyl, or where the R groups are joined to form an alkylene group.

"Aminocarbonylamino" refers to the group —NRC(O)NRR where each R is independently hydrogen, alkyl, aryl or cycloalkyl, or where two R groups are joined to form an alkylene group.

"Aminocarbonyloxy" refers to the group —OC(O)NRR where each R is independently hydrogen, alkyl, aryl or cycloalkyl, or where the R groups are joined to form an alkylene group.

"Amino-containing saccharide group" refers to a saccharide group having an amino substituent. Representative amino-containing saccharide include L-vancosamine, 3-desmethyl-vancosamine, 3-epi-vancosamine, 4-epi-vancosamine, acosamine, actinosamine, daunosamine, 3-epi-daunosamine, ristosamine, N-methyl-D-glucamine and the like.

"Aralkyl" or "arylalkyl" refers to an alkyl group, as defined above, substituted with one or more aryl groups, as defined above.

"Aryl" refers to a monovalent aromatic hydrocarbon group derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Particularly, an aryl group comprises from 6 to 14 carbon atoms.

"Aryloxy" refers to —O-aryl groups wherein "aryl" is as defined herein.

"Azido" refers to the radical —N$_3$.

"Carbohydrate" means a mono-, di-, tri-, or polysaccharide, wherein the polysaccharide can have a molecular weight of up to about 20,000, for example, hydroxypropyl-methylcellulose or chitosan. "Carbohydrate" also encompasses oxidized, reduced or substituted saccharide monoradical covalently attached to the anhydropyrimidine (e.g., anhydrothymidine or anhydrouridine), or derivative thereof any atom of the saccharide moiety, e.g., via the aglycone carbon atom. The "mono-, di-, tri-, or polysaccharide" can also include amino-containing saccharide groups. Representative "carbohydrate" include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose-, 2-O-(3-desmethyl-α-L-vancosaminyl)-β-D-glucopyranose, sucrose, lactose, or maltose; derivatives such as acetals, amines, acylated, sulfated and phosphorylated sugars; oligosaccharides having from 2 to 10 saccharide units. The saccharides can be either in their open or in their pyranose form.

"Carboxyl" refers to the radical —C(O)OH.

"Cyano" refers to the radical —CN.

"Cycloalkenyl" refers to cyclic hydrocarbyl groups having from 3 to 10 carbon atoms and having a single cyclic ring or multiple condensed rings, including fused and bridged ring systems and having at least one and particularly from 1 to 2 sites of olefinic unsaturation. Such cycloalkenyl groups include, by way of example, single ring structures such as cyclohexenyl, cyclopentenyl, cyclopropenyl, and the like.

"Cycloalkyl" refers to cyclic hydrocarbyl groups having from 3 to about 10 carbon atoms and having a single cyclic ring or multiple condensed rings, including fused and bridged ring systems, which optionally can be substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, and multiple ring structures such as adamantanyl, and the like.

"Heterocycloalkyl" refers to a stable heterocyclic non-aromatic ring and fused rings containing one or more heteroatoms independently selected from N, O and S. A fused heterocyclic ring system may include carbocyclic rings and need only include one heterocyclic ring. Examples of heterocyclic rings include, but are not limited to, piperazinyl, homopiperazinyl, piperidinyl and morpholinyl.

"Halo" or "halogen" refers to fluoro, chloro, bromo and iodo. "Halide" refers to any halogen including, F, Cl, I, or Br.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, cycloalkenyl, cycloheteroalkenyl, and the like having from 1 to 5, and particularly from 1 to 3 heteroatoms.

"Heteroaryl" refers to a monovalent heteroaromatic group derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. The heteroaryl group can be a 5-20 membered heteroaryl, or 5-10 membered heteroaryl. Particular heteroaryl groups are those derived from thiophen, pyrrole, benzothiophene, benzofuran, indole, pyridine, quinoline, imidazole, oxazole and pyrazine.

"Hydroxyl" refers to the radical —OH.

"Peptide" refers to a polyamino acid containing up to 2, 5, 10, or about 100 amino acid residues.

"Polypeptide" means polyamino acid containing from about 100 amino acid units to about 1,000 amino acid units, from about 100 amino acid units to about 750 amino acid units, or from about 100 amino acid units to about 500 amino acid units.

"Stereoisomer" as it relates to a given compound is well understood in the art, and refers to another compound having the same molecular formula, wherein the atoms making up the other compound differ in the way they are oriented in space, but wherein the atoms in the other compound are like the atoms in the given compound with respect to which atoms are joined to which other atoms (e.g. an enantiomer, a diastereomer, or a geometric isomer). See for example, Morrison and Boyd, Organic Chemistry, 1983, 4th ed., Allyn and Bacon, Inc., Boston, Mass., p. 123.

"Substituted" refers to a group in which one or more hydrogen atoms are each independently replaced with the same or different substituent(s). "Substituted" groups particularly refer to groups having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$. Typical substituents include, but are not limited to, —X, —R$^i$ (with the proviso that R$^i$ is not hydrogen), —O—, =O, —OR$^i$, —SR$^i$, —S$^-$, =S, —NR$^i$R$^{ii}$, =NR$^i$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^i$, —OS(O$_2$)O$^-$, —OS(O)$_2$R$^i$, —P(O)(O—)$_2$, —P(O)(OR$^i$)(O$^-$), —OP(O)(OR$^i$)(OR$^{ii}$), —C(O)R$^i$, —C(S)R$^i$, —C(O)OR$^i$, —C(O)NR$^i$R$^{ii}$, —C(O)O$^-$, —C(S)OR$^i$, —NR$^{iii}$C(O)NR$^i$R$^{ii}$, —NR$^{iii}$C(S)NR$^i$R$^{ii}$, —NR$^{iiii}$C(NR$^{iii}$)NR$^i$R$^{ii}$ and —C(NR$^{iii}$)NR$^i$R$^{ii}$, where each X is independently a halogen.

"Substituted amino" includes those groups recited in the definition of "substituted" herein, and particularly refers to the group —N(R)$_2$ where each R is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group.

"Sulfonyl" refers to the group —S(=O$_2$)—R.

"Thioalkoxy" refers to the group —S-alkyl.

"Thioaryloxy" refers to the group —S-aryl.

"Thioketo" refers to the group =S.

"Thiol" refers to the group —SH.

The terms "alkanol", "alkenol" and "alkynol", as used herein, refer to the alcohol versions of respective alkanes, alkenes and alkynes. The alcohols may contain one or more OH moieties. Furthermore, the alcohols may be branched or straight and the OH moieties may be present at the terminal carbons or elsewhere along the carbon chain. More than one OH group may be substituted at any particular carbon. Examples of "alkanols" are methanol, ethanol, CH$_3$CH(OH)$_2$, etc Examples of alkenols include CH$_2$CHOH, CH$_3$CH$_2$CHOH, etc. An example of an alkynol is CH$_3$CH$_2$CCOH. As used in the claims, a substitution of an alkanol implies that one of the hydrogens is removed at the linking atom and that atom is bonded to the entity having the substitution. The same interpretation applies to all other moieties described in this specification where the context requires such interpretation.

The term "amino sugar" refers to a sugar or saccharide that contains an amino group in place of a hydroxyl group. Derivatives of amino containing sugars, such as N-acetyl-glucosamine, N-acetyl mannosamine, N-acetyl galactosamine, N-acetyl neuraminic acid and sialic acids in general are examples of amino sugars.

The term "analog" or "analogue" refers to without limitation any compound which has structural similarity to the compounds of the present disclosure and would be expected, by one skilled in the art, to exhibit the same or similar utility as the claimed and/or referenced compounds.

The term "carrier" as used in the context of a carrier conjugated to a PSA de-N-acetylase inhibitor generally refers to a peptide or protein carrier, such as an antibody or antibody fragment.

The term "cell surface antigen" (or "cell surface epitope") refers to an antigen (or epitope) on surface of a cell that is extracellularly accessible at any cell cycle stage of the cell, including antigens that are predominantly or only extracellularly accessible during cell division. "Extracellularly accessible" in this context refers to an antigen that can be bound by an antibody provided outside the cell without need for permeabilization of the cell membrane.

The term "chemotherapy" as used herein refers to use of an agent (e.g., drug, antibody, etc.), particularly an agent(s) that is selectively destructive to a cancerous cell, in treatment of a disease, with treatment of cancer being of particular interest.

The term "conjugated" generally refers to a chemical linkage, either covalent or non-covalent, usually covalent, that proximally associates one molecule of interest with second molecule of interest.

The terms "cyclic" and "heterocyclic" refer to rings where, respectively, none or one or more of the carbon atoms have been replaced. For instance, for a "heterocyclic" ring, a carbon in the ring may be substituted with N, O, or S. Such atoms which are substituted are herein called "heteroatoms." One of skill in the art would recognize that other suitable heteroatoms exist. One having ordinary skill in the art will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

The term "de-N-acetyl sialic acid antigen" (which may also be referred to as "de-N-acetylated sialic acid antigen" or "deNAc SA antigen") refers to a compound having or mimicking a deNAc sialic acid epitope (deNAc SA epitope), which epitope is minimally defined by a dimer of residues of sialic acid or sialic acid derivative, where the dimer contains at least one de-N-acetylated sialic acid residue adjacent an N-acylated (e.g., acetylated or propionylated) sialic acid residue or a sialic acid derivative residue. Examples of de-N-acetyl sialic acid antigens are provided in the present disclosure, and include, without limitation, de-N-acetylated polysaccharide derivatives ("PS derivatives"), de-N-acetylated gangliosides, and de-N-acetylated derivatives of a sialic-acid modified protein, particularly a sialic-acid modified protein that is accessible at an extracellular surface of a mammalian cell, particularly a human cell, more particularly a cancer cell, particularly a human cancer cell. It should be noted that description of a deNAc SA antigen as a derivative of a starting molecule (e.g., PS derivative or ganglioside derivative) is not meant to be limiting as to the method of production of the de-N-acetyl sialic acid antigen, but rather is meant as a convenient way to describe the structure of the exemplary deNAc SA antigen.

The term "derivative" refers to without limitation any compound which has a structure derived from the structure of the compounds of the present disclosure and whose structure is sufficiently similar to those disclosed herein and based upon that similarity, would be expected, by one skilled in the art, to exhibit the same or similar activities and utilities as the claimed and/or referenced compounds.

The term "effective amount" of a compound as provided herein is intended to mean a non-lethal but sufficient amount of the compound to provide the desired utility. For instance, for inhibition of a polysialic acid de-N-acetylase, the effective amount is the amount which provides clinically meaningful inhibition of polysialic acid de-N-acetylase or complex in a subject. As will be pointed out below, the exact amount required will vary from subject to subject, depending on the species, age, and general condition of the subject, the severity of the condition or disease that is being treated, the particular compound used, its mode of administration, and the like. Thus, it is not possible to specify an exact "effective amount." However, an appropriate effective amount may be determined by one of ordinary skill in the art using only routine experimentation.

The term "immunotherapy" refers to treatment of disease (e.g., cancer) by modulating an immune response to a disease antigen. In the context of the present application, immunotherapy refers to providing an anti-cancer immune response in a subject by administration of an antibody (e.g., a monoclonal antibody) and/or by administration of an antigen the elicits an anti-tumor antigen immune response in the subject.

The term "inactivation" of a cell is used herein to indicate that the cell has been rendered incapable of cell division to form progeny. The cell may nonetheless be capable of response to stimulus and/or biosynthesis for a period of time, e.g., to provide for production of a cell surface molecule (e.g., cell surface protein or polysaccharide).

The term "in combination with" as used herein refers to uses where, for example, a first therapy is administered during the entire course of administration of a second therapy; where the first therapy is administered for a period of time that is overlapping with the administration of the second therapy, e.g. where administration of the first therapy begins before the administration of the second therapy and the administration of the first therapy ends before the administration of the second therapy ends; where the administration of the second therapy begins before the administration of the first therapy and the administration of the second therapy ends before the administration of the first therapy ends; where the administration of the first therapy begins before administration of the second therapy begins and the administration of the second therapy ends before the administration of the first therapy ends; where the administration of the second therapy begins before administration of the first therapy begins and the administration of the first therapy ends before the administration of the second therapy ends. As such, "in combination" can also refer to regimen involving administration of two or more therapies. "In combination with" as used herein also refers to administration of two or more therapies which may be administered in the same or different formulations, by the same or different routes, and in the same or different dosage form type.

The term "inhibitor" is intended to mean a compound that binds to an enzyme or complex and decreases its activity.

The term "inhibitors of polysialic acid de-N-acetylase" refers to without limitation any compound or composition that blocks, reduces or otherwise inhibits the de-N-acetylating of one or more N-acetyl neuraminic acid residues of polysialic acid.

The term "isolated" is intended to mean that a compound is separated from all or some of the components that accompany it in nature. "Isolated" also refers to the state of a compound separated from all or some of the components that accompany it during manufacture (e.g., chemical synthesis, recombinant expression, culture medium, and the like).

The term "monoclonal antibody" refers to an antibody composition having a homogeneous antibody population. The term is not limited by the manner in which it is made. The term encompasses whole immunoglobulin molecules, as well as Fab molecules, F(ab')2 fragments, Fv fragments, single chain fragment variable displayed on phage (scFv), fusion proteins comprising an antigen-binding portion of an antibody and a non-antibody protein, and other molecules that exhibit immunological binding properties of the parent monoclonal antibody molecule. Methods of making polyclonal and monoclonal antibodies are known in the art and described more fully below.

The term "pharmaceutically acceptable" refers to a material that is not biologically or otherwise undesirable, i.e., the material is of a medically acceptable quality and composition that may be administered to an individual along with the selected active pharmaceutical ingredient without causing any undesirable biological effects or interacting in a deleterious manner with any of the other components of the pharmaceutical composition in which it is contained.

The term "pharmaceutically acceptable excipient" as used herein refers to any suitable substance which provides a pharmaceutically acceptable vehicle for administration of a compound(s) of interest to a subject. "Pharmaceutically acceptable excipient" can encompass substances referred to as pharmaceutically acceptable diluents, pharmaceutically acceptable additives and pharmaceutically acceptable carriers.

The term "polysialic acid de-N-acetylase" is intended to mean an enzyme that catalyzes the reaction of de-N-acetylating one or more N-acetyl-neuraminic acid residues of polysialic acid.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like. Polypeptides may be of any size, and the term "peptide" refers to polypeptides that are 8-50 residues (e.g., 8-20 residues) in length.

The term "purified" is intended to mean a compound of interest has been separated from components that accompany it in nature and provided in an enriched form. "Purified" also refers to a compound of interest separated from components that can accompany it during manufacture (e.g., in chemical synthesis, recombinant expression, culture medium, and the like) and provided in an enriched form. Typically, a compound is substantially pure when it is at least 50% to 60%, by weight, free from organic molecules with which it is naturally associated or with which it is associated during manufacture. Generally, the preparation is at least 75%, more usually at least 90%, and generally at least 99%, by weight, of the compound of interest. A substantially pure compound can be obtained, for example, by extraction from a natural source (e.g., bacteria), by chemically synthesizing a compound, or by a combination of purification and chemical modification. A substantially pure compound can also be obtained by, for example, enriching a sample having a compound that binds an antibody of interest. Purity can be measured by any appropriate method, e.g., chromatography, mass spectroscopy, HPLC analysis, etc.

The term "SEAM 3-reactive antigen" refers to an antigen having an epitope that is specifically bound by the monoclonal antibody (mAb) SEAM 3 (ATCC Deposit No. HB-12170). Exemplary SEAM 3-reactive antigens are provided in the working examples.

The terms "saturation" and "unsaturation" are used to describe whether, between a particular pair of atoms, a single or double bond exists. Single bonds are termed "saturations" and double bonds are termed "unsaturations." One of skill in the art would recognize that triple bonds could also constitute "unsaturations". Furthermore, the terms "saturated" and "partially unsaturated" and "Fully unsaturated" are used to refer to the presence or lack of unsaturations in a particular ring. For instance, cyclohexane would be considered a "saturated" compound. On the other hand cyclohexene would be "partially unsaturated" due to the presence of one unsaturation. Finally, benzene is "fully unsaturated" due to the presence of the maximum, three, unsaturations.

The term "substrate inhibitor" is intended to mean a compound that is an analog or derivative of a natural substrate of an enzyme or complex that binds to and decreases its activity.

The term "subject" is intended to cover humans, mammals and other animals which contain polysialic acid in any fashion. The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

In the context of cancer therapies and diagnostics described herein, "subject" or "patient" is used interchangeably herein to refer to a subject having, suspected of having, or at risk of developing a tumor, where the cancer is one associated with cancerous cells expressing a poly sialic de-N-acetylase. Samples obtained from such subject are likewise suitable for use in the methods of the present disclosure.

The term "transition state analogue" refers to a substrate designed to mimic the properties or the geometry of the transition state of a reaction.

As used herein, the terms "determining," "measuring," and "assessing," and "assaying" are used interchangeably and include both quantitative and qualitative determinations.

It is further noted that the claims may be drafted to exclude any optional or alternative element. As such, this statement is intended to serve as antecedent basis for use of such exclusive terminology as "solely", "only" and the like in connection with the recitation of claim elements, or the use of a "negative" limitation.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

In further describing the invention, exemplary methods and compounds employable therein are described first in greater detail, followed by a review of the various compositions (e.g., formulations, kits, etc.) that may find use in such methods, as well as a discussion of various representative applications in which the methods and compositions find use.

Methods and Compounds

As summarized above, the present disclosure provides methods of administering an inhibitor of PSA de-N-acetylase to a subject in need thereof, e.g., for the treatment of a host suffering from disease or condition treatable by an inhibitor of PSA de-N-acetylase (as described in greater detail below).

One feature of the methods of the present disclosure is that the inhibitor agents disclosed herein find particular use in inhibiting the growth of cancerous cells in a subject. This method involves administering to the subject an effective amount of a pharmaceutically acceptable formulation that comprises an inhibitor of PSA de-N-acetylase. Administering of the PSA de-N-acetylase facilitates a reduction in viability of cancerous cells exposed to the inhibitor. An advantage of this method is that the PSA de-N-acetylase inhibitor is cytotoxic to cancer cells containing the PSA de-acetylase enzyme. Thus inhibition of the enzyme in cancer cells has the effect of retarding or otherwise arresting cell growth, and even inducing apoptosis, leading to cell death. In certain embodiments, the cytotoxicity of the PSA de-N-acetylase inhibitors of the present disclosure is dose dependent, and thus adjustable. Specific examples of cancerous cells amenable to treatment by the subject methods include melanoma, leukemia, or neuroblastoma.

In a related embodiment, the subject being treated possesses a deNAc SA epitope. The epitope can be present inside a cell or expressed on the cell surface, such as a cancer cell. This aspect can be beneficial in that cells expressing or presenting a deNAc SA epitope can be more amenable to treatment with a PSA de-N-acetylase inhibitor of the present disclosure. Of course the PSA de-N-acetylase inhibitor can be administered to a subject that is naïve with respect to the deNAc SA epitope, for example, where therapy is initiated at a point where presence of the epitope is not detectable, and thus is not intended to be limiting. It is also possible to initiate PSA de-N-acetylase inhibitor therapy prior to the first sign of disease symptoms, at the first sign of possible disease, or prior to or after diagnosis of a primary cancer and/or metastases of a cancer having a detectable deNAc SA epitope (e.g., a ganglioside or other glycoconjugate that is at least partially de-N-acetylated).

Another embodiment involves screening for the deNAc SA epitope in combination with PSA de-N-acetylase inhibitor therapy. In this method, cells from a subject undergoing treatment, or being tested for susceptibility to treatment, with a PSA de-N-acetylase inhibitor are screened for the presence of a deNAc SA epitope. This can be accomplished using an antibody or antibody fragment that binds to the epitope (e.g., a SEAM 3 monoclonal antibody (ATCC Deposit No. HB-12170)). As with cancer therapies in general, an advantage of this approach is the ability to select individuals with a cellular proliferation disorder or stage of disorder likely to be more responsive to PSA de-N-acetylase inhibitor therapy compared to those that are not. Another advantage of targeting a subject with cells bearing a deNAc SA epitope is that progress over the treatment course can be monitored, and therapy, including dosing regimens, amounts and the like can be adjusted accordingly.

In practicing the methods disclosed herein, routes of administration (path by which the PSA de-N-acetylase inhibitor is brought into contact with the body) may vary, where representative routes of administration for the PSA de-N-acetylase inhibitor are described in greater detail below. In certain embodiments, the PSA de-N-acetylase inhibitor is administered by infusion or by local injection. It also can be administered prior, at the time of, or after other therapeutic interventions, such as surgical intervention to remove cancerous cells. The PSA de-N-acetylase inhibitor can also be administered as part of a combination therapy, in which at least one of an immunotherapy, a cancer chemotherapy or a radiation therapy is administered to the subject (as described in greater detail below).

In the methods of the present disclosure, an effective amount of a PSA de-N-acetylase inhibitor is administered to a subject in need thereof. In particular, PSA de-N-acetylase inhibitors of specific interest are those that inhibit growth of a cancer cell in a host when the compounds are administered in an effective amount according to the present disclosure. The amount administered varies depending upon the goal of the administration, the health and physical condition of the individual to be treated, age, the taxonomic group of individual to be treated (e.g., human, non-human primate, primate, etc.), the degree of resolution desired, the formulation of the PSA de-N-acetylase inhibitor composition, the treating clinician's assessment of the medical situation, and other relevant factors. It is expected that the amount will fall in a relatively broad range that can be determined through routine trials. For example, the amount of PSA de-N-acetylase inhibitor employed to inhibit cancer cell growth is not more than about the amount that could otherwise be irreversibly toxic to the subject (i.e., maximum tolerated dose). In other cases the amount is around or even well below the toxic threshold, but still in an inhibitory concentration range, or even as low as threshold dose.

Individual doses are typically not less than an amount required to produce a measurable effect on the subject, and may be determined based on the pharmacokinetics and pharmacology for absorption, distribution, metabolism, and excretion ("ADME") of the PSA de-N-acetylase inhibitor, and thus based on the disposition of the compound within the subject. This includes consideration of the route of administration as well as dosage amount, which can be adjusted for topical (applied directly where action is desired for mainly a local effect), enteral (applied via digestive tract for systemic or local effects when retained in part of the digestive tract), or parenteral (applied by routes other than the digestive tract for systemic or local effects) applications.

Disposition of the compound and its corresponding biological activity within a subject is typically gauged against the fraction of PSA de-N-acetylase inhibitor present at a target of interest. For example, an inhibitor once administered can accumulate as a component of polysialic acid, a glycoconjugate or other biological target that concentrates the inhibitor material in cancer cells and cancerous tissue. Thus dosing regimens in which the compound is administered so as to accumulate in a target of interest over time can be part of a strategy to allow for lower individual doses. This can also mean that the dose of compounds that are cleared more slowly in vivo can be lowered relative to the inhibitory concentration calculated from in vitro assays (e.g., effective amount in vitro approximates mM concentration, versus less than mM concentrations in vivo).

As an example, the effective amount of a dose or dosing regimen can be gauged from the IC50 of a given PSA de-N-acetylase inhibitor. By "IC50" is intended the concentration of a drug required for 50% inhibition in vitro. Alternatively, the effective amount can be gauged from the EC50 of a given PSA de-N-acetylase inhibitor. By "EC50" is intended the plasma concentration required for obtaining 50% of a maximum effect in vivo.

In general, with respect to the inhibitors of the present disclosure, an effective amount is usually not more than 200× the calculated IC50. Typically, the amount of a PSA de-N-acetylase inhibitor that is administered is less than about 200×, less than about 150×, less then about 100× and many embodiments less than about 75×, less than about 60×, 50×, 45×, 40×, 35×, 30×, 25×, 20×, 15×, 10× and even less than about 8× or 2× than the calculated IC50. In one embodiment, the effective amount is about 1× to 50× of the calculated IC50, and sometimes about 2× to 40×, about 3× to 30× or about 4× to 20× of the calculated IC50. In other embodiments, the effective amount is the same as the calculated IC50, and in certain embodiments the effective amount is an amount that is more than the calculated IC50.

In other embodiments, an effect amount is not more than 100× the calculated EC50. For instance, the amount of a PSA de-N-acetylase inhibitor that is administered is less than about 100×, less than about 50×, less than about 40×, 35×, 30×, or 25× and many embodiments less than about 20×, less than about 15× and even less than about 10×, 9×, 9×, 7×, 6×, 5×, 4×, 3×, 2× or 1× than the calculated EC50. In one embodiment, the effective amount is about 1× to 30× of the calculated EC50, and sometimes about 1× to 20×, or about 1× to 10× of the calculated EC50. In other embodiments, the effective amount is the same as the calculated EC50, and in certain embodiments the effective amount is an amount that is more than the calculated EC50.

Effective amounts can readily be determined empirically from assays, from safety and escalation and dose range trials, individual clinician-patient relationships, as well as in vitro and in vivo assays such as those described herein and illustrated in the Experimental section, below.

As noted above, another feature of the subject methods is that the PSA de-N-acetylase inhibitor can be administered to the subject in combination with one or more other therapies. For example, a therapy or treatment other than administration of a PSA de-N-acetylase inhibitor composition can be administered anywhere from simultaneously to up to 5 hours or more, e.g., 10 hours, 15 hours, 20 hours or more, prior to or after the PSA de-N-acetylase inhibitor. In certain embodiments, the PSA de-N-acetylase inhibitor and other therapeutic intervention are administered or applied sequentially, e.g., where the PSA de-N-acetylase inhibitor is administered before or after another therapeutic treatment. In yet other embodiments, the inhibitor and other therapy are administered simultaneously, e.g., where the PSA de-N-acetylase inhibitor and a second therapy are administered at the same time, e.g., when the second therapy is a drug it can be administered along with the PSA de-N-acetylase inhibitor as two separate formulations or combined into a single composition that is administered to the subject. Regardless of whether administered sequentially or simultaneously, as illustrated above, the treatments are considered to be administered together or in combination.

PSA de-N-acetylase inhibitors which find use in the present methods and may be present in the subject compositions include, but are not limited to those with appropriate specificity and potency for inhibiting PSA de-N-acetylase so as to affect the growth of a cancer cell. As such, inhibitors of PSA de-N-acetylase with high specificity and potency aid the compound in achieving the intended end result of modifying cellular proliferation while minimizing unwanted side effects and toxicity. Put differently, the PSA de-N-acetylase inhibitors employed in the methods and compositions of the present disclosure need not be identical to those disclosed in the Examples section below, so long as the subject PSA de-N-acetylase inhibitors are able to inhibit growth of a cancerous cell. Thus, one of skill will recognize that a number of derivatives (described in more detail below), can be made without substantially affecting the activity of the PSA de-N-acetylase inhibitors. This includes inhibitor compositions of pharmaceutically acceptable salts (e.g., hydrochloride, sulfate salts), solvates (e.g., mixed ionic salts, water, organics), hydrates (e.g., water), and prodrug forms thereof (e.g., esters, acetyl forms), anomers (e.g., α/β mutarotation), tautomers (e.g., keto-enol tautomerism) and stereoisomers (e.g., α-D-isomer). It also includes various inhibitor compositions that contain one or more immunogenic excipients, such as an adjuvant, carrier and the like, as well as non-immunogenic inhibitor compositions that are essentially devoid of adjuvant or other immunogenic excipients.

PSA de-N-acetylase inhibitors of specific interest are substrate inhibitors of PSA de-N-acetylase. As such, the binding of a substrate inhibitor to a PSA de-N-acetylase can block the enzyme (or an enzyme complex) from catalyzing its normal reaction. Inhibitor binding is either reversible or irreversible. Irreversible inhibitors of the present disclosure can react with the enzyme and change it chemically (e.g., suicide inhibitor via covalent ligation). These inhibitors modify key amino acid residues needed for enzymatic activity of the PSA de-N-acetylase. In contrast, reversible inhibitors bind non-covalently and different types of inhibition are produced depending on whether these inhibitors bind the enzyme, the enzyme-substrate complex, or both. Other reversible inhibitors bind to a portion of the enzyme complex, intermediate or pathway component and compete for substrate directly or indirectly, thereby altering PSA de-N-acetylase activity. The PSA de-N-acetylase inhibitors can include any type of inhibitor that achieves the intended end result.

In certain embodiments, the subject methods employ a PSA de-N-acetylase substrate inhibitor that is an N-substituted derivative of an amino sugar. In a specific embodiment, the substrate inhibitor is a monomer of an N-substituted amino sugar. In another specific embodiment, the substrate inhibitor is an N-substituted hexosamine or a neuraminic acid. In yet another specific embodiment, the hexosamine is an N-substituted derivative of mannosamine, glucosamine or galactosamine.

Conjugates are also contemplated. The PSA de-N-acetylase inhibitors may be conjugated to one or more various secondary molecules that impart additional characteristics to the inhibitor. For example, the N-substituted derivative of an amino sugar may be a conjugate of two or more molecules. As such, in one embodiment, the inhibitor comprises a conjugate. An advantage of inhibitors that are conjugated to another molecule includes the ability to retain the inhibitory activity, while exploiting properties of the second molecule of the conjugate to impart an additional desired characteristic. For example, the inhibitor can be conjugated to a second molecule such as a peptide, polypeptide, lipid, carbohydrate and the like that aids in solubility, storage or other handling properties, cell permeability, half-life, controls release and/or distribution such as by targeting a particular cell (e.g., neurons, leucocytes etc.) or cellular location (e.g., lysosome, endosome, mitochondria etc.), tissue or other bodily location (e.g., blood, neural tissue, particular organs etc.). Other examples include the conjugation of a dye, fluorophore or other detectable labels or reporter molecules for assays, tracking and the like.

More specifically, the PSA de-N-acetylase inhibitors described herein can be conjugated to a second molecule such as a peptide, polypeptide, dye, fluorophore, nucleic acid, carbohydrate, lipid and the like (e.g., at either the reducing or non-reducing end), such as the attachment of a lipid moiety, including N-fatty acyl groups such as N-lauroyl, N-oleoyl, fatty amines such as dodecyl amine, oleoyl amine, and the like (e.g., see U.S. Pat. No. 6,638,513)). In a particular embodiment, the conjugate comprises a monomer of substrate inhibitor. As such, the conjugate can be composed of (1) a first molecule comprising a PSA de-N-acetylase substrate inhibitor that is a monomer of an amino sugar, and (2) a second molecule that is devoid of the amino sugar monomer. Also included is a polymeric PSA conjugate. By "polymeric PSA conjugate" is intended a polymer composed of one or more monomers of a PSA de-N-acetylase inhibitor. The conjugate can be a non-immunogenic composition comprising a polymeric PSA conjugate. By "non-immunogenic composition" is intended a composition that is elicits no or little (e.g., is essentially devoid of) adjuvant or other immunogenic excipients. Also included is a conjugate of a PSA de-N-acetylase inhibitor devoid of a deNAc SA epitope. Thus the conjugate of a PSA de-N-acetylase substrate inhibitor can be one that is missing a deNAc SA epitope.

By a "deNAc SA epitope" is intended a molecule that has (i) maximal cross-reactivity with an antibody against polysialic acid in which one or more residues is a de-N-acetyl neuraminic acid residue, and (ii) has minimal to no cross-reactivity with an antibody against normal polysialic acid, especially as presented on a non-cancerous mammalian, e.g., human, cell surface. Thus the minimal deNAc SA epitope is a disaccharide of sialic acid residues in which one or both residues contain a free amine at the C5 amino position; when one of the two residues is de-N-acetylated, the second residue contains an N-acetyl group (but, in some embodiments, not an N-propionyl group). The disaccharide unit defining this minimal epitope may be at the reducing end, the non-reducing end, or within a polymer of sialic acid residues (e.g., within a polysaccharide). De-N-acetylated residues in the context of PSA containing N-acylated residues are immunogenic and elicit antibodies that are reactive with the deNAc SA epitope, but are minimally reactive or not detectably reactive with human PSA antigens. For example, the de-N-acetylated NmB polysaccharide epitope was identified using a murine anti-N-propionyl *Neisseria meningitidis* group B (N—Pr NmB) polysaccharide mAb (monoclonal antibodies), SEAM 3, described in Granoff et al., 1998, J Immunol 160:5028 (anti-N—Pr NmB PS mAbs); U.S. Pat. No. 6,048,527 (anti-NmB antibodies); and U.S. Pat. No. 6,350,449 (anti-NmB antibodies).

In a specific exemplary embodiment, the subject conjugate modifies cellular uptake relative to unconjugated inhibitor. In a related embodiment, the PSA de-N-acetylase inhibitor conjugate increases cellular uptake relative to unconjugated inhibitor. In other embodiments, the conjugate decreases cellular uptake relative to unconjugated inhibitor. In this aspect, the efficiency of cellular uptake can be increased or decreased by linking to peptides or proteins that facilitate endocytosis. For example, a given PSA de-N-acetylase inhibitor can be linked to a ligand for a target receptor or large molecule that is more easily engulfed by endocytotic mechanisms, such as an antibody. The antibody or other ligand can then be internalized by endocytosis and the payload released by acid hydrolysis or enzymatic activity when the endocytotic vesicle fuses with lysosomes. As such, the conjugate may be one that increases endocytosis relative to unconjugated substrate inhibitor. To decrease cellular uptake, the conjugate can include a ligand that retains the inhibitor on the surface of a cell, which can be useful as a control for cellular uptake, or in some instances decrease uptake in one cell type while increasing it in others. In a specific example, passive transport of N-substituted amino sugar derived inhibitor can be facilitated by acylating the OH groups of the amino sugar with, for example, acetyl groups (Collins et al Glycobiology 2000, 10:11). Also, even though there are no known transporters of N-acyl mannosamine and N-acyl neuraminic acid (or poly N-acyl neuraminic acid) on the surface of human cells, all can enter the cell by endocytosis, for example, receptor mediated endocytosis, non-receptor mediated endocytosis, or pinocytosis (Bardor et al J. Biol. Chem. 2005, 280:4228). The endocytotic vesicles fuse with lysozomes that contain membrane transporters for N-acetyl hexosamines and N-acetyl neuraminic acid (the Michaelis constant, Km, for forming a substrate/transporter complex for the N-acetyl hexosamine transporters is 4.4 mM, and for N-acetyl neuraminic acid is ~0.5 mM) ("Essentials of Glycobiology" Ed. Varki et al, Cold Spring Harbor Press, NY 1999). Thus, modification of the inhibitors by conjugation can exploit the endocytosis system for cellular uptake.

Another embodiment is a composition comprising an aggregate of one or more monomers of a PSA de-N-acetylase inhibitor as disclosed herein. By "aggregate" is intended a particle comprising an aggregated complex of individual monomers of a molecule and having a combined molecular weight that is a multiple of the molecular weight of an individual monomer of the complex. For example, an aggregate of one or more monomers of a PSA de-N-acetylase inhibitor include an aggregate complex having a particle molecular weight that is 10× or more of the molecular weight of an individual monomer in the aggregated monomer complex. This includes an aggregate having a particle with a molecular weight of greater than about 50,000, to greater than about 250,000 Daltons, to greater than 500,000 Daltons, to greater than 750,000 Daltons, to greater than 1,000,000 Daltons up to a particle having a uniform particle size that is readily visible by light microscopy, e.g., under a standard low magnification light microscope (e.g., 40× magnification).

Thus, the aggregate can be a molecular or microscopic particle. For microscopic particles, the optimal aggregate for a desired use can be selected by varying the mean aggregate diameter, e.g., 1 um to 20 μm, and usually about or smaller than the diameter of a cell targeted for exposure and uptake of the material of interest, e.g., cells are usually approximately 1-20 μm in diameter. For non-visible molecular particles, as well as the microscopic particles, the desired aggregate can be selected by measuring uptake and internalized by cells. In each instance, the aggregate of the PSA de-N-acetylase inhibitor is capable of being taken up and internalized by cells better than non-aggregated inhibitor relative to each other, a control, and/or both, including as measured by inhibition of cell growth.

The aggregate can be formed by admixing monomers of one or more PSA de-N-acetylase inhibitors under aggregating conditions, by degradation or hydrolysis of a polymeric PSA conjugate under aggregating conditions, or a combination thereof. By "aggregating condition" is intended chemical-physical conditions that cause an otherwise soluble material to form an aggregated substance in solution. For instance a polymeric PSA conjugate, such a poly alpha (2→8) N-substituted neuraminic acid, can be treated with an exo-neuraminidase and heated (e.g., 30° C.-70° C.) for an appropriate period of time (e.g., 1 hr to overnight) so as to form an aggregate. Treatment with exoneuramidase enriches for non-reducing end de-N-acetyl residues which aggregate when heated forming particles that are readily taken up by cells. This also includes addition of one or more excipients that are capable of facilitating aggregation of the substance of interest. Of particular interest aggregating substances such as aluminum hydroxide.

Other features of the subject conjugates can include one where the conjugate reduces toxicity relative to unconjugated inhibitor. In further embodiments, the conjugate targets a cancer cell relative to unconjugated inhibitor. Additional examples include a conjugate the PSA de-N-acetylase inhibitor with one or more molecules that complement, potentiate, enhance or can otherwise operate synergistically in connection with the inhibitor. For instance, the PSA de-N-acetylase inhibitors can optionally have attached an anti-cancer drug for delivery to a site of a cancer cell to further facilitate tumor killing or clearance, e.g., an anti-proliferation moiety (e.g., VEGF antagonist, e.g., an anti-VEGF antibody), a toxin (e.g., an anti-cancer toxin, e.g., ricin, *Pseudomonas* exotoxin A, and the like), radionuclide (e.g. $^{90}$Y, $^{131}$I, $^{177}$L, $^{10}$B for boron neutron capture, and the like), anti-cancer drugs (e.g. doxorubicin, calicheamicin, maytansinoid DM1, auristatin caupecitabine, 5-fluorouricil, leucovorin, irinotercan, and the like), and/or can optionally be modified to provide for improved pharmacokinetic profile (e.g., by PEGylation, hyperglycosylation, and the like).

As noted above, the PSA de-N-acetylase substrate inhibitors derived from hexosamine and neuraminic acid are of particular importance. In certain embodiments, the PSA de-N-acetylase inhibitor is an N-substituted hexosamine compound of formula (I), or an N-substituted neuraminic acid compound of formula (II):

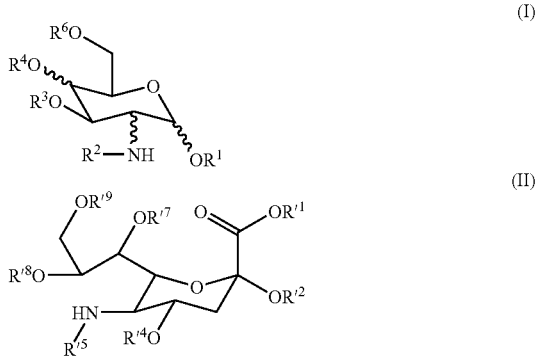

or the pharmaceutically acceptable salts, solvates, hydrates, and prodrug forms thereof, anomers, tautomers and stereoisomers thereof. In formula (I) and (II), —NH—$R^2$ and —NH—$R'^5$ comprise an inhibitor of an amide bond hydrolysis reaction catalyzed by said PSA de-N-acetylase; and each $R^1$, $R'^1$, $R'^2$, $R^3$, $R^4$, $R'^4$, $R^6$, $R'^7$, $R'^8$ and $R'^9$ is independently hydrogen or a substituted or unsubstituted moiety selected from the group consisting of: heteroatom, alkyl, aryl, cycloalkyl, heteroaryl, alkenyl, acyl, sulfonyl, carbohydrate, lipid, nucleic acid, peptide, dye, fluorophore and polypeptide.

Thus is certain embodiments, the compound is of formula (I) or (II), and —NH—$R^2$ and —NH—$R'^5$ comprise an inhibitor of an amide bond hydrolysis reaction catalyzed by the PSA de-N-acetylase. By "inhibitor of an amide bond hydrolysis reaction catalyzed by the PSA de-N-acetylase" is intended an amide bond mimetic or analogue that is resistant to cleavage and removal by a PSA de-N-acetylase. For example, the enzymatic mechanism of N-acetyl group removal from natural substrates of amino hydrolases is facilitated by attack by a nucleophile in the enzyme active site on the amide carbonyl group, resulting in formation and collapse of a tetrahedral intermediate followed cleavage of the amide bond. Also, all chemical transformations pass through an unstable structure called the transition state, which is poised between the chemical structures of the substrates and products. An accepted view of enzymatic catalysis is tight binding to the unstable transition state structure. Thus inhibitors that block the transformation state ("transition state inhibitor") also are contemplated by the present disclosure, as they can bind tightly to the enzyme by capturing a fraction of the binding energy for the transition state species and disrupt or inhibit native substrate conversion to product (See, e.g., Schramm, V L (1998) Annu Rev Biochem. 67:693-720).

Accordingly, specific inhibitors of PSA de-N-acetylase of the present disclosure include those that inhibit the amide bond hydrolysis reaction catalyzed by the PSA de-N-acetylase. They include substrate inhibitors in general, as well as specific transition state inhibitors. Of particular interest are —NH—$R^2$ and —NH—$R'^5$ moieties that approximate the geometric and chemical features of methylacetamide (i.e., N-acetyl group on native substrate), and thus fit into and disrupt the enzyme substrate binding site. Examples include —NH—$R^2$ and —NH—$R'^5$ moieties that comprise components reactive with nucleophiles (e.g., acryl, methacryl, haloacetyl), or mimic the structure of the tetrahedral intermediate (e.g., methanesulfonyl, di and tri-halo acetyl).

Additional —NH—$R^2$ and —NH—$R'^5$ moieties, and specifically, $R^2$ and $R'^5$ groups for use in the method and compositions of the present disclosure include, but are not necessarily limited to, carbamates, amides, N-alkyl and N-aryl amines, imine derivatives, enamine derivatives, N-sulfonyls, and the like. Further exemplary $R^2$ and $R'^5$ groups include, but are not necessarily limited to: acyl types such as formyl, trifluoroacetyl, phthalyl, and p-toluenesulfonyl; aromatic carbamate types such as benzyloxycarbonyl (Cbz) and substituted benzyloxy-carbonyls, 1-(p-biphenyl)-1-methylethoxycarbonyl, and 9-fluorenylmethyloxycarbonyl (Fmoc); aliphatic carbamate types such as tert-butyloxycarbonyl (tBoc), ethoxycarbonyl, diisopropylmethoxycarbonyl, and allyloxycarbonyl; cyclic alkyl carbamate types such as cyclopentyloxycarbonyl and adamantyloxycarbonyl; alkyl types such as triphenylmethyl and benzyl; trialkylsilane such as trimethylsilane; and thiol containing types such as phenylthiocarbonyl and dithiasuccinoyl. Further exemplary $R^2$ and $R'^5$ groups of interest include haloacetyls such as mono-, di- and trihaloacetylys (e.g., trihaloacyl groups, such as trihaloacetyl and trihalopropionyl groups (e.g., trichloroacetyl, trifluoroacetyl, trichloropriopionyl, trifluoropriopionyl)), and the like.

Compounds of specific interest are those of formula (I) or formula (II) where $R^2$ and $R'^5$ are selected from haloacetyl, acyl and sulfonyl. In a specific embodiment, compounds of formula (I) or formula (II) include those where $R^2$ and $R'^5$ are a haloacetyl that is a radical selected from —C(O)CH$_2$F, —C(O)CH$_2$Cl, —C(O)CH$_2$Br, —C(O)CH$_2$I, —C(O)CHF$_2$, —C(O)CHCl$_2$, —C(O)CHBr$_2$, —C(O)CF$_3$, —C(O)CCl$_3$, and —C(O)CBr$_3$; where $R^2$ and $R'^5$ is an acyl that is a radical selected from —C(O)CH=CH$_2$ and —C(O)C(=CH$_2$)(CH$_3$); and where $R^2$ and $R'^5$ is a sulfonyl that is a radical selected from —S(=O)$_2$(CH$_3$).

In certain embodiments, the compound is of formula (I), and $R^1$, $R'^1$, $R'^2$, $R^3$, $R^4$, $R'^4$, $R^6$, $R'^7$, $R'^8$ and $R'^9$ are each independently hydrogen, $C_1$-$C_{18}$ alkyl, $C_1$-$C_{18}$ alkenyl or $C_1$-$C_{18}$ acyl, where the alkyl, alkenyl or acyl is linear or branched, and optionally substituted with a hydroxyl, an ester and its derivatives, a carboxyl and its derivatives, a cycloalkyl, a heterocycloalkyl, an aryl, a heteroaryl, an aralkyl, a heteroatom, and possibly containing in-chain or bridging heteroatoms such as nitrogen, oxygen and sulfur.

For example, when one or more of $R^1$, $R'^1$, $R'^2$, $R^3$, $R^4$, $R'^4$, $R^6$, $R'^7$, $R'^8$ and $R'^9$ comprise an acyl group, which includes a saturated or unsaturated acyl group, they are usually a saturated or unsaturated $C_{2-18}$ acyl group, a saturated or unsaturated $C_{2-16}$ acyl group, a saturated or unsaturated $C_{2-12}$ acyl group, a saturated or unsaturated $C_{2-10}$ acyl group, a saturated or unsaturated $C_{2-8}$ acyl group, a saturated or unsaturated $C_{2-6}$ acyl group, a saturated or unsaturated $C_{2-4}$ acyl group, or a saturated $C_{2-4}$ acyl group. A saturated acyl group as used herein is intended to refer to a carbonyl joined to a saturated alkyl group; an unsaturated acyl group as used herein is intended to refer to a carbonyl joined to an unsaturated alkyl group. In some embodiments, unsaturated acyl groups are of particular interest.

Of specific interest are compounds depicted in Table I.

TABLE 1

The compound is an N-substituted hexosamine of formula (I), and $R^1$, $R^4$, $R^5$, and $R^6$ are each independently absent, counter ion/salt, hydrogen or acyl (e.g., acetyl).

| Compound | Name | $R^3$ |
|---|---|---|
| Ia | N-Acryl Hexosamine | —C(O)CH=CH$_2$ |
| Ib | N-Methacryl Hexosamine | —C(O)C(=CH$_2$)(CH$_3$) |
| Ic | N-Fluoroacetyl Hexosamine | —C(O)CH$_2$F |
| Id | N-Chloroacetyl Hexosamine | —C(O)CH$_2$Cl |
| Ie | N-Bromoacetyl Hexosamine | —C(O)CH$_2$Br |
| If | N-Iodoacetyl Hexosamine | —C(O)CH$_2$I |
| Ig | N-Methyanesulfonyl Hexosamine | —S(=O)$_2$(CH$_3$) |
| Ih | N-Difluoroacetyl Hexosamine | —C(O)CHF$_2$ |
| Ii | N-Dichloroacetyl Hexosamine | —C(O)CHCl$_2$ |
| Ij | N-Dibromoacetyl Hexosamine | —C(O)CHBr$_2$ |
| Ik | N-Trifluoroacetyl Hexosamine | —C(O)CF$_3$ |
| IL | N-Trichloroacetyl Hexosamine | —C(O)CCl$_3$ |
| Im | N-Tribromoacetyl Hexosamine | —C(O)CBr$_3$ |

In another specific embodiment, the inhibitor compounds are those depicted in Table 2.

TABLE 2

The compound is an N-substituted neuraminic acid of formula (II), and $R'^1$, $R'^2$, $R'^4$, $R'^7$, $R'^8$ and $R'^9$ are each independently absent, counter ion/salt, or hydrogen.

| Compound | Name | $R^5$ |
|---|---|---|
| IIa | N-Acryl Neuraminic Acid | —C(O)CH=CH$_2$ |
| IIb | N-Methacryl Neuraminic Acid | —C(O)C(=CH$_2$)(CH$_3$) |
| IIc | N-Fluoroacetyl Neuraminic Acid | —C(O)CH$_2$F |
| IId | N-Chloroacetyl Neuraminic Acid | —C(O)CH$_2$Cl |
| IIe | N-Bromoacetyl Neuraminic Acid | —C(O)CH$_2$Br |
| IIf | N-Iodoacetyl Neuraminic Acid | —C(O)CH$_2$I |
| IIg | N-Methyanesulfonyl Neuraminic Acid | —S(=O)$_2$(CH$_3$) |
| IIh | N-Difluoroacetyl Neuraminic Acid | —C(O)CHF$_2$ |
| IIi | N-Dichloroacetyl Neuraminic Acid | —C(O)CHCl$_2$ |
| IIj | N-Dibromoacetyl Neuraminic Acid | —C(O)CHBr$_2$ |
| IIk | N-Trifluoroacetyl Neuraminic Acid | —C(O)CF$_3$ |
| IIL | N-Trichloroacetyl Neuraminic Acid | —C(O)CCl$_3$ |
| IIm | N-Tribromoacetyl Neuraminic Acid | —C(O)CBr$_3$ |

In a particular embodiment, the hexosamine compound of formula (I) is selected from a mannosamine compound of formula (III), a galactosamine compound of formula (IV), or a glucosamine compound of formula (V):

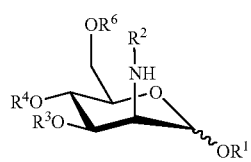

(III)

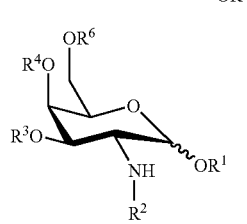

(IV)

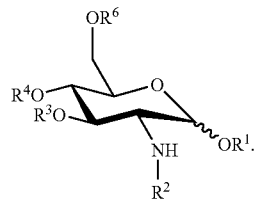

(V)

wherein each $R^1$, $R^2$, $R^3$, $R^4$, and $R^6$ are as defined above for formula (I) and Formula (II).

Of particular interested are PSA de-N-acetylase inhibitors where the compound is a mannosamine compound of formula (III), a galactosamine compound of formula (IV), or a glucosamine compound of formula (V), where each $R^1$, $R^3$, $R^4$ and $R^6$ is independently selected from hydrogen and substituted or unsubstituted acyl.

In other embodiments, the compound is a mannosamine compound of formula (III), a galactosamine compound of formula (IV), or a glucosamine compound of formula (V), where each $R^2$ is independently selected from a radical of the group consisting of —C(O)CH=CH$_2$, —C(O)C(=CH$_2$)(CH$_3$), —C(O)CH$_2$F, —C(O)CH$_2$Cl, —C(O)CH$_2$Br, —C(O)CH$_2$I, —S(=O)$_2$(CH$_3$), —C(O)CHF$_2$, —C(O)CHCl$_2$, —C(O)CHBr$_2$, —C(O)CF$_3$, —C(O)CCl$_3$, and —C(O)CBr$_3$.

In a specific embodiment, the compound is a mannosamine compound of formula (III), a galactosamine compound of formula (IV), or a glucosamine compound of formula (V), where each $R^1$, $R^3$, $R^4$ and $R^6$ is independently selected from hydrogen and substituted or unsubstituted acyl, and each $R^2$ is independently selected from a radical of the group consisting of —C(O)CH=CH$_2$, —C(O)C(=CH$_2$)(CH$_3$), —C(O)CH$_2$F, —C(O)CH$_2$Cl, —C(O)CH$_2$Br, —C(O)CH$_2$I, —S(=O)$_2$(CH$_3$), —C(O)CHF$_2$, —C(O)CHCl$_2$, —C(O)CHBr$_2$, —C(O)CF$_3$, —C(O)CCl$_3$, and —C(O)CBr$_3$.

Of specific interest are the PSA de-N-acetylase inhibitors depicted in Table 3.

TABLE 3

The compound is an N-substituted hexosamine of formula (I), and $R^1$, $R^3$, $R^4$, and $R^6$ are each independently absent, counter ion/salt, or hydrogen.

| Compound | Name | $R^2$ |
|---|---|---|
| Ia1 | N-Acryl Mannosamine | —C(O)CH=CH$_2$ |
| Ia2 | N-Acryl Galactosamine | —C(O)CH=CH$_2$ |
| Ia3 | N-Acryl Glucosamine | —C(O)CH=CH$_2$ |
| Ib1 | N-Methacryl Mannosamine | —C(O)C(=CH$_2$)(CH$_3$) |
| Ib2 | N-Methacryl Galactosamine | —C(O)C(=CH$_2$)(CH$_3$) |
| Ib3 | N-Methacryl Glucosamine | —C(O)C(=CH$_2$)(CH$_3$) |
| Ic1 | N-Fluoroacetyl Mannosamine | —C(O)CH$_2$F |
| Ic2 | N-Fluoroacetyl Galactosamine | —C(O)CH$_2$F |
| Ic3 | N-Fluoroacetyl Glucosamine | —C(O)CH$_2$F |
| Id1 | N-Chloroacetyl Mannosamine | —C(O)CH$_2$Cl |
| Id2 | N-Chloroacetyl Galactosamine | —C(O)CH$_2$Cl |
| Id3 | N-Chloroacetyl Glucosamine | —C(O)CH$_2$Cl |
| Ie1 | N-Bromoacetyl Mannosamine | —C(O)CH$_2$Br |
| Ie2 | N-Bromoacetyl Galactosamine | —C(O)CH$_2$Br |
| Ie3 | N-Bromoacetyl Glucosamine | —C(O)CH$_2$Br |
| If1 | N-Iodoacetyl Mannosamine | —C(O)CH$_2$I |
| If2 | N-Iodoacetyl Galactosamine | —C(O)CH$_2$I |
| If3 | N-Iodoacetyl Glucosamine | —C(O)CH$_2$I |
| Ig1 | N-Methyanesulfonyl Mannosamine | —S(=O)$_2$(CH$_3$) |
| Ig2 | N-Methyanesulfonyl Galactosamine | —S(=O)$_2$(CH$_3$) |
| Ig3 | N-Methyanesulfonyl Glucosamine | —S(=O)$_2$(CH$_3$) |
| Ih1 | N-Difluoroacetyl Mannosamine | —C(O)CHF$_2$ |
| Ih2 | N-Difluoroacetyl Galactosamine | —C(O)CHF$_2$ |

TABLE 3-continued

The compound is an N-substituted hexosamine of formula (I), and $R^1$, $R^3$, $R^4$, and $R^6$ are each independently absent, counter ion/salt, or hydrogen.

| Compound | Name | $R^2$ |
|---|---|---|
| Ih3 | N-Difluoroacetyl Glucosamine | —C(O)CHF$_2$ |
| Ii1 | N-Dichloroacetyl Mannosamine | —C(O)CHCl$_2$ |
| Ii2 | N-Dichloroacetyl Galactosamine | —C(O)CHCl$_2$ |
| Ii3 | N-Dichloroacetyl Glucosamine | —C(O)CHCl$_2$ |
| Ij1 | N-Dibromoacetyl Mannosamine | —C(O)CHBr$_2$ |
| Ij2 | N-Dibromoacetyl Galactosamine | —C(O)CHBr$_2$ |
| Ij3 | N-Dibromoacetyl Glucosamine | —C(O)CHBr$_2$ |
| Ik1 | N-Trifluoroacetyl Mannosamine | —C(O)CF$_3$ |
| Ik2 | N-Trifluoroacetyl Galactosamine | —C(O)CF$_3$ |
| Ik3 | N-Trifluoroacetyl Glucosamine | —C(O)CF$_3$ |
| Il1 | N-Trichloroacetyl Mannosamine | —C(O)CCl$_3$ |
| Il2 | N-Trichloroacetyl Galactosamine | —C(O)CCl$_3$ |
| Il3 | N-Trichloroacetyl Glucosamine | —C(O)CCl$_3$ |
| Im1 | N-Tribromoacetyl Mannosamine | —C(O)CBr$_3$ |
| Im2 | N-Tribromoacetyl Galactosamine | —C(O)CBr$_3$ |
| Im3 | N-Tribromoacetyl Glucosamine | —C(O)CBr$_3$ |

As noted above, in certain embodiments, the present disclosure features a polymeric PSA conjugate that comprises two or more monomeric units of a PSA de-N-acetylase inhibitor as disclosed herein. Of particular interest is a polymeric PSA conjugate that comprises one or more N-substituted neuraminic acid residues. A specific example is poly alpha (2→8) N-substituted neuraminic acid of formula III, where $R'^1$, $R'^2$, $R'^4$, $R'^5$, $R'^7$, $R'^8$ and $R'^9$ are as defined above, and n is a positive integer.

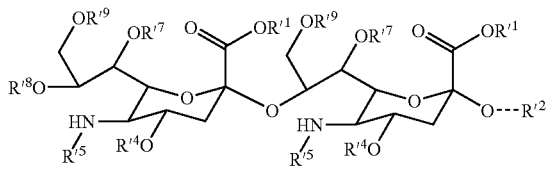

(III)

Thus poly alpha (2→8) N-substituted neuraminic acid of formula III is composed of one or more N-substituted neuraminic acid residues that is capable of inhibiting (or being converted to an inhibitor) of a PSA de-N-acetylase. The poly alpha (2→8) N-substituted neuraminic acid derivatives find particular use in the present disclosure as a precursor for conversion to N-substituted neuraminic acid derivatives of formula II by hydrolysis or treatment with a sialidase. For instance, where the compound is of formula III, and n=0, then the compound is a compound of formula II. The monomeric forms of the N-substituted neuraminic acid derivatives according to formula II may be better since they are taken up by a specific transporter with a Km lower than the N-acyl hexosamine transporters. Also, the N-substituted neuraminic acid derivatives can be incorporated into newly synthesized PSA whereas the polymeric PSA conjugates may be appended directly to glycoconjugates.

Specific polymeric PSA inhibitors of interest are depicted in Table 4.

TABLE 4

The compound is an N-substituted poly alpha (2→8) neuraminic acid of formula (III), and $R'^1$, $R'^2$, $R'^4$, $R'^7$, $R'^8$ and $R'^9$ are each independently absent, counter ion/salt, or hydrogen, and n = 1 to 200.

| Compound | Name | $R'^6$ |
|---|---|---|
| IIIa | Poly alpha (2→8) N-Acryl Neuraminic Acid | —C(O)CH=CH$_2$ |
| IIIb | Poly alpha (2→8) N-Methacryl Neuraminic Acid | —C(O)C(=CH$_2$)(CH$_3$) |
| IIIc | Poly alpha (2→8) N-Fluoroacetyl Neuraminic Acid | —C(O)CH$_2$F |
| IIId | Poly alpha (2→8) N-Chloroacetyl Neuraminic Acid | —C(O)CH$_2$Cl |
| IIIe | Poly alpha (2→8) N-Bromoacetyl Neuraminic Acid | —C(O)CH$_2$Br |
| IIIf | Poly alpha (2→8) N-Iodoacetyl Neuraminic Acid | —C(O)CH$_2$I |
| IIIg | Poly alpha (2→8) N-Methyanesulfonyl Neuraminic Acid | —S(=O)$_2$(CH$_3$) |
| IIIh | Poly alpha (2→8) N-Difluoroacetyl Neuraminic Acid | —C(O)CHF$_2$ |
| IIIi | Poly alpha (2→8) N-Dichloroacetyl Neuraminic Acid | —C(O)CHCl$_2$ |
| IIIj | Poly alpha (2→8) N-Dibromoacetyl Neuraminic Acid | —C(O)CHBr$_2$ |
| IIIk | Poly alpha (2→8) N-Trifluoroacetyl Neuraminic Acid | —C(O)CF$_3$ |
| IIIL | Poly alpha (2→8) N-Trichloroacetyl Neuraminic Acid | —C(O)CCl$_3$ |
| IIIm | Poly alpha (2→8) N-Tribromoacetyl Neuraminic Acid | —C(O)CBr$_3$ |

Thus, exemplary compounds of the present disclosure include those where the PSA de-N-acetylase inhibitor comprises an N-substituted hexosamine selected from: N-acryl mannosamine; N-acryl galactosamine; N-acryl glucosamine; N-methacryl mannosamine; N-methacryl galactosamine; N-methacryl glucosamine; N-fluoroacetyl mannosamine; N-fluoroacetyl galactosamine; N-fluoroacetyl glucosamine; N-chloroacetyl mannosamine; N-chloroacetyl galactosamine; N-chloroacetyl glucosamine; N-bromoacetyl mannosamine; N-bromoacetyl galactosamine; N-bromoacetyl glucosamine; N-iodoacetyl mannosamine; N-iodoacetyl galactosamine; N-iodoacetyl glucosamine; N-methyanesulfonyl mannosamine; N-methyanesulfonyl galactosamine; N-methyanesulfonyl glucosamine; N-difluoroacetyl mannosamine; N-difluoroacetyl galactosamine; N-difluoroacetyl glucosamine; N-dichloroacetyl mannosamine; N-dichloroacetyl galactosamine; N-dichloroacetyl glucosamine; N-dibromoacetyl mannosamine; N-dibromoacetyl galactosamine; N-dibromoacetyl glucosamine; N-trifluoroacetyl mannosamine; N-trifluoroacetyl galactosamine; N-trifluoroacetyl glucosamine; N-trichloroacetyl mannosamine; N-trichloroacetyl galactosamine; N-trichloroacetyl glucosamine; N-tribromoacetyl mannosamine; N-tribromoacetyl galactosamine; and N-tribromoacetyl glucosamine; or the pharmaceutically acceptable salts, solvate, hydrates, and prodrug forms thereof, anomers, tautomers and stereoisomers thereof, and derivatives thereof.

Other exemplary compounds are those where the PSA de-N-acetylase inhibitor comprises an N-substituted neuraminic acid selected from the group consisting of: N-acryl neuraminic acid; N-methacryl neuraminic acid; N-fluoroacetyl neuraminic acid; N-chloroacetyl neuraminic acid; N-bromoacetyl neuraminic acid; N-iodoacetyl neuraminic acid; N-methyanesulfonyl neuraminic acid; N-difluoroacetyl neuraminic acid; N-dichloroacetyl neuraminic acid; N-dibromoacetyl neuraminic acid; N-trifluoroacetyl neuraminic acid; N-trichloroacetyl neuraminic acid; and N-tribromoacetyl neuraminic acid; or the pharmaceutically acceptable salts, solvate, hydrates, and prodrug forms thereof, anomers, tautomers and stereoisomers thereof, and derivatives thereof.

Compounds exemplifying the polymeric PSA inhibitors are those selected from the group consisting of: poly alpha (2→8) N-acryl neuraminic acid; poly alpha (2→8) N-methacryl neuraminic acid; poly alpha (2→8) N-fluoroacetyl neuraminic acid; poly alpha (2→8) N-chloroacetyl neuraminic acid; poly alpha (2→8) N-bromoacetyl neuraminic acid; poly alpha (2→8) N-iodoacetyl neuraminic acid; poly alpha (2→8) N-methanesulfonyl neuraminic acid; poly alpha (2→8) N-difluoroacetyl neuraminic acid; poly alpha (2→8) N-dichloroacetyl neuraminic acid; poly alpha (2→8) N-dibromoacetyl neuraminic acid; poly alpha (2→8) N-trifluoroacetyl neuraminic acid; poly alpha (2→8) N-trichloroacetyl neuraminic acid; and poly alpha (2→8) N-tribromoacetyl neuraminic acid; or the pharmaceutically acceptable salts, solvate, hydrates, and prodrug forms thereof, anomers, tautomers and stereoisomers thereof, and derivatives thereof.

The PSA de-N-acetylase inhibitor compounds of the present disclosure may be in compositions that contain single isomers and mixtures thereof, including stereoisomers, mixtures of stereoisomers, as well various derivatives thereof that can occur as equilibrium mixtures of anomers and/or tautomers. For instance, N-substituted hexosamines according to formula (I) include three stereo centers with respect to the pyranos ring, which includes the α and β anomers in addition to the D configuration that is depicted. Examples of stereoisomers of the compounds of the present disclosure include the α-D-isomer, α-L-isomer, β-D-isomer, and β-L-isomer, as well as tautomers and mixtures including α,β-D-isomers, α,β-L-isomers, α-DL-isomers, and β-DL-isomers. Thus in one embodiment, compositions are provided that consist essentially of a stereoisomer of N-substituted hexosamine that is a α-D-isomer, α-L-isomer, β-D-isomer, or an β-L-isomer.

Isomers exhibiting improved activity on a molar basis or improved specificity with respect to interfering with PSA de-N-acetylase activity are a specifically featured in the present disclosure. Of particular interest are the various isomers of the PSA de-N-acetylase inhibitors that exhibit improved activity on a molar basis, or improved specificity with respect to arresting cell growth, reducing cell viability and/or inducing apoptosis. Examples include the N-substituted α-D-hexosamine derivatives of the present disclosure, such as α-D-mannosamine, α-D-galactosamine, and α-D-glucosamine, as compared to β-D-mannosamine, β-D-galactosamine, and β-D-glucosamine. Other examples are mixtures of stereoisomers, such as the N-substituted anomers αβ-D-mannosamine, αβ-D-galactosamine, and αβ-D-glucosamine. Such compounds can be readily selected for this purpose by comparing against a matrix of isomeric test compounds, and cell based assays using various cancerous cell lines, such as described in the Experimental section below.

The present disclosure also includes prodrugs of the PSA de-N-acetylase inhibitors disclosed herein. Such prodrugs are in general functional derivatives of the compounds that are readily convertible in vivo into the required compounds. Thus, in the methods of the present disclosure, the term "administering" encompasses administering the compound specifically disclosed or with a compound which may not be specifically disclosed, but which converts to the specified compound in vivo after administration to the subject in need thereof. Conventional procedures for the selection and preparation of suitable prodrug derivatives are described, e.g., in Wermuth, "Designing Prodrugs and Bioprecursors" in Wermuth, ed. The Practice of Medicinal Chemistry, 2d Ed., pp. 561-586 (Academic Press 2003). Prodrugs include esters that hydrolyze in vivo (e.g., in the human body) to produce a compound described herein suitable for the methods and compositions of the present disclosure. Suitable ester groups include, without limitation, those derived from pharmaceutically acceptable, aliphatic carboxylic acids, particularly alkanoic, alkenoic, cycloalkanoic and alkanedioic acids, in which each alkyl or alkenyl moiety has no more than 6 carbon atoms. Illustrative esters include formates, acetates, propionates, butyrates, acrylates, citrates, succinates, and ethylsuccinates.

Whether or not a given PSA de-N-acetylase inhibitor or conjugate thereof is suitable for use according to the present disclosure can be readily determined using various inhibitor assays, such as those employed in the Experimental section, below. Generally, an PSA de-N-acetylase inhibitor is suitable for use in the subject methods if it inhibits growth of a target cell by at least about 2 to 10-fold, usually by at least about 50-fold and sometimes by at least about 100-fold to 200-fold relative to a normal control cell, as determined using the cell based assays, such as those described in the Experimental section, below. In certain embodiments, a PSA de-N-acetylase inhibitor is one that reduces viability of a target cell (such as a particular cancer cell or cell line), arrests growth and/or induces apoptosis of a target cell, and/or induces cell death, as observed in the cell-based assays described in the Experimental section below.

Methods of Production

The PSA de-N-acetylase inhibitors and derivatives thereof can be conventionally prepared by techniques known to one of skill in the art, including as described herein and in the Examples. Representative references describing various synthesis approaches, intermediates, precursors, analysis, as well as the synthesis and preparation of conjugates, diagnostics and the like, include U.S. Pat. Nos. 4,315,074; 4,395,399; 4,719,289; 4,806,473; 4,874,813; 4,925,796; 5,180,674; 5,246,840; 5,262,312; 5,278,299; 5,288,637; 5,369,017; 5,677,285; 5,780,603; 5,876,715; 6,040,433; 6,133,239; 6,242,583; 6,271,345; 6,323,339; 6,406,894; 6,476,191; 6,538,117; 6,797,522; 6,927,042; 6,953,850; 7,067,623; and 7,129,333; the disclosures of which are herein incorporated by reference. See also, the following references: "Solid Support Oligosaccharide Synthesis and Combinatorial Carbohydrate Libraries," Peter H. Seeberger Ed, Wiley-Interscience, John Wiley & Sons, Inc, NY, 2001; Plante et al., Science (2001) 291(5508):1523; Marcaurelle et al., Glycobiology, 2002, 12(6): 69R-77R; Sears et al., Science (2001) 291:2344-2350; Bertozzi et al., Chemical Glycobiology (2001) Science 291:2357-2364; MacCoss et al., Org. Biomol. Chem., 2003, 1:2029; and Liang et al. Science (1996) 274(5292):1520; Kayser et al J. Biol. Chem. 1992 267:16934, Keppler et al Glycobiology 2001, 11:11R; Luchansky et al Meth. Enzymol. 2003, 362:249; Oetke et al Eur. J. Biochem. 2001, 268: 4553; and WO/1997/045436; the disclosures of which are herein incorporated by reference.

Pharmaceutically acceptable salts of the PSA de-N-acetylase inhibitors and derivatives thereof can be prepared by treating the free acid with an appropriate amount of a pharmaceutically acceptable base. Representative pharmaceutically acceptable bases are ammonium hydroxide, sodium hydroxide, potassium hydroxide, lithium hydroxide, calcium hydroxide, magnesium hydroxide, ferrous hydroxide, zinc hydroxide, copper hydroxide, aluminum hydroxide, ferric hydroxide, isopropylamine, trimethylamine, diethylamine, triethylamine, tripropylamine, ethanolamine, 2-dimethylaminoethanol, 2-diethylaminoethanol, lysine, arginine, histidine, and the like. The reaction is conducted in water, alone or in combination with an inert, water-miscible organic solvent, at a temperature of from about 0° C. to about 100° C., and can be at room temperature. The molar ratio of compounds of general structure I to base used are chosen to provide the ratio desired for any particular salts. For preparing, for example, the ammonium salts of the free acid starting material, the starting material can be treated with approximately one equivalent of pharmaceutically acceptable base to yield a neutral salt. When calcium salts are prepared, approximately one-half a molar equivalent of base is used to yield a neutral salt, while for aluminum salts, approximately one-third a molar equivalent of base will be used.

Pharmaceutical Formulations

Also provided are pharmaceutical compositions containing the PSA de-N-acetylase inhibitors employed in the subject methods. The term "PSA de-N-acetylase inhibitor composition" is used herein as a matter of convenience to refer generically to compositions comprising an inhibitor of PSA de-N-acetylase, including conjugates. PSA de-N-acetylase inhibitor compositions can comprise a PSA de-N-acetylase inhibitor, conjugate thereof, or both. Compositions useful for modifying the growth of cells, particularly cancer cells, are contemplated by the present disclosure.

The PSA de-N-acetylase inhibitor compositions, e.g., in the form of a pharmaceutically acceptable salt, can be formulated for oral, topical or parenteral administration for use in the subject methods, as described above. In certain embodiments, e.g., where a PSA de-N-acetylase inhibitor is administered as a liquid injectable (such as in those embodiments where they are administered intravenously or directly into a tissue), a PSA de-N-acetylase inhibitor formulation is provided as a ready-to-use dosage form, or as a reconstitutable storage-stable powder or liquid composed of pharmaceutically acceptable carriers and excipients.

Methods for producing and formulating PSA de-N-acetylase inhibitors suitable for administration to a subject (e.g., a human subject) are well known in the art. For example, PSA de-N-acetylase inhibitors can be provided in a pharmaceutical composition comprising an effective amount of a PSA de-N-acetylase inhibitor and a pharmaceutical excipients (e.g., saline). The pharmaceutical composition may optionally include other additives (e.g., buffers, stabilizers, preservatives, and the like). An effective amount of PSA de-N-acetylase inhibitor is generally an amount effective to provide for enhancing an anti-cancer response in a subject for a desired period. A therapeutic goal (e.g., reduction in tumor load) can be accomplished by single or multiple doses under varying dosing regimen.

By way of illustration, the PSA de-N-acetylase inhibitor compositions can be admixed with conventional pharmaceutically acceptable carriers and excipients (i.e., vehicles) and used in the form of aqueous solutions, tablets, capsules, elixirs, suspensions, syrups, wafers, patches and the like. Such pharmaceutical compositions contain, in certain embodiments, from about 0.1 to about 90% by weight of the active compound, and more generally from about 1 to about 30% by weight of the active compound. The pharmaceutical compositions may contain common carriers and excipients, such as corn starch or gelatin, lactose, dextrose, sucrose, microcrystalline cellulose, kaolin, mannitol, dicalcium phosphate, sodium chloride, and alginic acid. Disintegrators commonly used in formulations include croscarmellose, microcrystalline cellulose, corn starch, sodium starch glycolate and alginic acid.

A liquid composition will generally consist of a suspension or solution of the compound or pharmaceutically acceptable salt in a suitable liquid carrier(s), for example, ethanol, glycerine, sorbitol, non-aqueous solvent such as polyethylene glycol, oils or water, with a suspending agent, preservative, surfactant, wetting agent, flavoring or coloring agent. Alternatively, a liquid formulation can be prepared from a reconstitutable powder.

For example, a powder containing active compound, suspending agent, sucrose and a sweetener can be reconstituted with water to form a suspension; and a syrup can be prepared from a powder containing active ingredient, sucrose and a sweetener.

A composition in the form of a tablet can be prepared using any suitable pharmaceutical carrier(s) routinely used for preparing solid compositions. Examples of such carriers include magnesium stearate, starch, lactose, sucrose, microcrystalline cellulose and binders, for example, polyvinylpyrrolidone. The tablet can also be provided with a color film coating, or color included as part of the carrier(s). In addition, active compound can be formulated in a controlled release dosage form as a tablet comprising a hydrophilic or hydrophobic matrix.

A composition in the form of a capsule can be prepared using routine encapsulation procedures, for example, by incorporation of active compound and excipients into a hard gelatin capsule. Alternatively, a semi-solid matrix of active compound and high molecular weight polyethylene glycol can be prepared and filled into a hard gelatin capsule; or a solution of active compound in polyethylene glycol or a suspension in edible oil, for example, liquid paraffin or fractionated coconut oil can be prepared and filled into a soft gelatin capsule.

Tablet binders that can be included are acacia, methylcellulose, sodium carboxymethylcellulose, poly-vinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. Additionally, it may be desirable to add a coloring agent to make the dosage form more attractive in appearance or to help identify the product.

The compounds of the present disclosure and their pharmaceutically acceptable salts that are active when given parenterally can be formulated for intramuscular, intrathecal, or intravenous administration.

A typical composition for intramuscular or intrathecal administration will be of a suspension or solution of active ingredient in an oil, for example, arachis oil or sesame oil. A typical composition for intravenous or intrathecal administration will be a sterile isotonic aqueous solution containing, for example, active ingredient and dextrose or sodium chloride, or a mixture of dextrose and sodium chloride. Other examples are lactated Ringer's injection, lactated Ringer's plus dextrose injection, Normosol-M and dextrose, Isolyte E, acylated Ringer's injection, and the like. Optionally, a co-solvent, for example, polyethylene glycol, a chelating agent, for example, ethylenediamine tetracetic acid, and an anti-oxidant, for example, sodium metabisulphite may be included in the formulation. Alternatively, the solution can be freeze dried and then reconstituted with a suitable solvent just prior to administration.

The compounds of the present disclosure and their pharmaceutically acceptable salts which are active on rectal administration can be formulated as suppositories. A typical suppository formulation will generally consist of active ingredient with a binding and/or lubricating agent such as a gelatin or cocoa butter or other low melting vegetable or synthetic wax or fat.

The compounds disclosed herein and their pharmaceutically acceptable salts which are active on topical administration can be formulated as transdermal compositions or transdermal delivery devices ("patches"). Such compositions include, for example, a backing, active compound reservoir, a control membrane, liner and contact adhesive. Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. No. 5,023,252, herein incorporated by reference in its entirety. Such patches may be constructed for continuous, pulsatile, or on demand delivery of pharmaceutical agents.

In certain embodiments of interest, the PSA de-N-acetylase inhibitor composition is administered as a single pharmaceutical formulation. It also may be administered with an effective amount of another agent that includes other suitable compounds and carriers, and also may be used in combination with other active agents. The present disclosure, therefore, also includes pharmaceutical compositions comprising pharmaceutically acceptable excipients. The pharmaceutically acceptable excipients include, for example, any suitable vehicles, adjuvants, carriers or diluents, and are readily available to the public. The pharmaceutical compositions of the present disclosure may further contain other active agents as are well known in the art.

One skilled in the art will appreciate that a variety of suitable methods of administering a formulation of the present disclosure to a subject or host, e.g., patient, in need thereof, are available, and, although more than one route can be used to administer a particular formulation, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The subject formulations of the present disclosure can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Suppository formulations are also provided by mixing with a variety of bases such as emulsifying bases or water-soluble bases. Formulations suitable for vaginal administration may be presented as pessaries, tampons, creams, gels, pastes, foams.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present disclosure calculated in an amount sufficient to produce the desired effect in association with a pharmaceutically acceptable diluent, carrier or vehicle. The specifications for the novel unit dosage forms of the present disclosure depend on the particular compound employed and the effect to be achieved, and the pharmacodynamics associated with each compound in the host.

Those of skill in the art will readily appreciate that dose levels can vary as a function of the specific compound, the nature of the delivery vehicle, and the like. Suitable dosages for a given compound are readily determinable by those of skill in the art by a variety of means.

Optionally, the pharmaceutical composition may contain other pharmaceutically acceptable components, such a buffers, surfactants, antioxidants, viscosity modifying agents, preservatives and the like. Each of these components is well-known in the art. See, e.g., U.S. Pat. No. 5,985,310, the disclosure of which is herein incorporated by reference.

Other components suitable for use in the formulations of the present disclosure can be found in Remington's Pharmaceutical Sciences, Mack Pub. Co., 18th edition (June 1995). In an embodiment, the aqueous cyclodextrin solution further comprise dextrose, e.g., about 5% dextrose.

Utility: Exemplary Applications

The subject methods find use in a variety of applications, where in many applications the methods are modulating at least one cellular function, such as PSA de-N-acetylase mediation of polysialic acid structure and inhibition of cancerous cell growth. In this respect, the subject methods and composition find use in treating cellular proliferation disorders. Thus, a representative therapeutic application is the treatment of cellular proliferative disease conditions in general, e.g., cancers and related conditions characterized by abnormal cellular proliferation concomitant. Such disease conditions include cancer/neoplastic diseases and other diseases characterized by the presence of unwanted cellular proliferation, e.g., hyperplasias, and the like. As indicated, cellular proliferation disorders include those that abnormally express the deNAc SA epitope, which can be determined using anti-deNAc SA antibody or derivatives thereof. Of particular interest are antibodies that have the antigen binding specificity of the mAb SEAM 3. Examples of such antibodies include those having a light chain polypeptide comprising CDR1, CDR2 and CDR3 of the variable region of a SEAM 3 light chain polypeptide and a heavy chain polypeptide comprising CDR1, CDR2, and CDR3 of the variable region of the SEAM 3 heavy chain polypeptide. Such antibodies include chimeric antibodies, humanized antibodies, and the like.

By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease, e.g., so as to decrease tumor load, which decrease can include elimination of detectable cancerous cells; and/or (iii) relief, that is, causing the regression of clinical symptoms.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Thus the subject methods find use in, among other applications, the treatment of cellular proliferative disease conditions in which an effective amount of the PSA de-N-acetylase inhibitor is administered to the subject in need thereof. Treatment is used broadly as defined above, e.g., to include prevention or at least an amelioration in one or more of the symptoms of the disease, as well as a complete cessation thereof, as well as a reversal and/or complete removal of the disease condition, e.g., cure.

Compositions of the present disclosure can comprise a therapeutically effective amount of PSA de-N-acetylase inhibitor, as well as any other compatible components, as needed. By "therapeutically effective amount" is meant that the administration of that amount to an individual, either in a single dose, as part of a series of the same or different PSA de-N-acetylase inhibitor compositions, is effective to inhibit the growth of a cancerous cell in a subject. Such therapeutically effective amount of PSA de-N-acetylase inhibitor and its impact on cell growth includes cooperative and/or synergistic inhibition of cell growth in conjunction with one or more other therapies (e.g., immunotherapy, chemotherapy, radiation therapy etc.) As noted below, the therapeutically effective amount can be adjusted in connection with dosing regimen and diagnostic analysis of the subject's condition (e.g., monitoring for the present or absence of a cell surface epitopes using a SEAM 3 antibody) and the like.

The amount administered to an animal, particularly a human, in the context of the present disclosure should be sufficient to affect a prophylactic or therapeutic response in the animal over a reasonable time frame, and varies depending upon the goal of the administration, the health and physical condition of the individual to be treated, age, the taxonomic group of individual to be treated (e.g., human, non-human primate, primate, etc.), the degree of resolution desired, the formulation of the PSA de-N-acetylase inhibitor composition, the treating clinician's assessment of the medical situation, and other relevant factors. One skilled in the art will also recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Thus it is expected that the amount will fall in a relatively broad range, but can nevertheless be routinely determined through various features of the subject such as note above.

Also, suitable doses and dosage regimens can be determined by comparisons to anticancer or immunosuppressive agents that are known to affect the desired growth inhibitory or immunosuppressive response. Such dosages include dosages which result in the low dose inhibition of PSA de-N-acetylase, without significant side effects. In proper doses and with suitable administration of certain compounds, the present disclosure provides for a wide range of intracellular effects, e.g., from partial inhibition to essentially complete inhibition of PSA de-N-acetylase. This is especially important in the context of the present disclosure, as this differential inhibition can potentially be used to discriminate between cancer cells and highly proliferative non-malignant cells. Dosage treatment may be a single dose schedule or a multiple dose schedule (e.g., including ramp and maintenance doses). As indicated, the PSA de-N-acetylase inhibitor composition may be administered in conjunction with other agents, and thus doses and regiments can vary in this context as well to suit the needs of the subject.

The compositions of the present disclosure can be provided in a pharmaceutically acceptable excipient, which can be a solution such as an aqueous solution, often a saline solution, or they can be provided in powder form. The PSA de-N-acetylase inhibitor compositions may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of PSA de-N-acetylase inhibitors of the present disclosure in the pharmaceutical formulations can vary from less than about 0.1%, usually at or at least about 2% to as much as 20% to 50% or more by weight, and will be selected primarily by fluid volumes, viscosities, etc., in accordance with the particular mode of administration selected and the patient's needs. The resulting compositions may be in the form of a solution, suspension, tablet, pill, capsule, powder, gel, cream, lotion, ointment, aerosol or the like.

The PSA de-N-acetylase inhibitor (which may be optionally conjugated) can be used alone or in combination with other therapies (e.g., other anti-cancer agents). When used in combination, the various compositions can be provided in the same or different formulations. Where administered in different formulations, the compositions can be administered at the same or different dosage regimen (e.g., by the same or different routes, at the same or different time (e.g., on the same or different days)), and the like). In general, administration of the PSA de-N-acetylase inhibitor can be performed serially, at the same time, or as a mixture, as described in more detail below. Administration can be serial, with repeated doses of PSA de-N-acetylase inhibitor. Exemplary dosage regimens are described below in more detail.

In general, administration of a PSA de-N-acetylase inhibitor composition is accomplished by any suitable route, including administration of the composition orally, bucally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remington's Pharmaceutical Science, 18th ed., Mack Publishing Company, NY (1995).

It is recognized that when administered orally, PSA de-N-acetylase inhibitors should be protected from digestion. This is typically accomplished either by complexing the PSA de-N-acetylase inhibitor with a composition to render it resistant to acidic and enzymatic hydrolysis or by packaging in an appropriately resistant carrier such as a liposome. Means of protecting a compound of interest from digestion are well known in the art.

In order to enhance serum half-life, the PSA de-N-acetylase inhibitor preparations that are injected may also be encapsulated, introduced into the lumen of liposomes, prepared as a colloid, or other conventional techniques may be employed which provide an extended serum half-life. A variety of methods are available for preparing liposomes, as described in, e.g., Szoka et al., Ann. Rev. Biophys. Bioeng. 9:467 (1980), U.S. Pat. Nos. 4,235,871, 4,501,728 and 4,837,028. The preparations may also be provided in controlled release or slow-release forms for release and administration of the PSA de-N-acetylase inhibitor preparations as a mixture or in serial fashion.

The compositions also can be administered to subject that is at risk of disease to prevent or at least partially arrest the development of disease and its complications. A subject is "at risk" where, for example, the subject exhibits one or more signs or symptoms of disease, but which are insufficient for certain diagnosis and/or who has been or may be exposed to conditions that increase the probability of disease. For example, the PSA de-N-acetylase inhibitor compositions can also be administered to subject that is at risk of a cancer, has a cancer, or is at risk of metastasis of a cancer having a cell surface deNAc SA epitope (e.g., a cell surface ganglioside that is at least partially de-N-acetylated).

PSA de-N-acetylase inhibitor compositions are administered to a host in a manner that provides for the inhibition of growth of a cancerous cell, which may include monitor cell histology, viability, biological marker profile and the like (e.g., monitoring for the presence or absence of selective deNAc SA epitopes etc.). PSA de-N-acetylase inhibitor compositions can be administered serially or overlapping to maintain a therapeutically effective amount as believed needed for the desired end result (e.g., inhibition of cancerous cell growth). Typically, each dose and the timing of its administration is generally provided in an amount that is tolerated by the health of the subject, and can be based on IC50 and/or the EC50 as noted above. Thus amounts can vary widely for a given treatment.

Therapeutic response to the dose or treatment regime may be determined by known methods (e.g. by obtaining serum from the individual before and after the initial immunization, and demonstrating a change in the individual's status as noted above, for example an immunoprecipitation assay, or an ELISA, or a bactericidal assay, or a Western blot, or flow cytometric assay, or the like). The dosing may include washout periods to allow for clearance of the initial material, followed by halting or resumption of treatment. Thus dosage strategies can be modified accordingly.

In one embodiment, a PSA de-N-acetylase inhibitor composition is administered at least once, usually at least twice, and in some embodiments more than twice. In a related embodiment, the PSA de-N-acetylase inhibitor composition is administered in combination along a dosing schedule and course in conjunction with chemotherapy. In another embodiment, the PSA de-N-acetylase inhibitor composition is administered in combination with a dosing schedule and course in conjunction with immunotherapy. In yet another embodiment, the PSA de-N-acetylase inhibitor composition is administered in combination with a dosing schedule and course in conjunction with radiation therapy. Each individual dose of the PSA de-N-acetylase inhibitor composition may be administered before, during or after the complementary therapy such as immunotherapy, chemotherapy, or radiation therapy. As can be appreciated, combination therapies using a PSA de-N-acetylase inhibitor composition may be adjusted for a given end need.

Exemplary Cancer Therapies

The PSA de-N-acetylase inhibitors find use in a variety of cancer therapies (including cancer prevention and post-diagnosis cancer therapy) in a mammalian subject, particularly in a human. Subjects having, suspected of having or at risk of developing a tumor are contemplated for therapy and diagnosis described herein. Samples obtained from such subject are likewise suitable for use in the methods of the present disclosure.

More particularly, PSA de-N-acetylase inhibitor compositions described herein can be administered to a subject (e.g. a human patient) to, for example, facilitate reduction of viability of cancerous cells, e.g., to reduce tumor size, reduce tumor load, and/or improve the clinical outcome in patients. In particular, PSA de-N-acetylase inhibitor compositions can be used to disrupt the cell cycle of the cancer cell, and facilitate entry of the cell into apoptosis, e.g., by inducing cancerous cells to enter the pre-$G_0$ cell cycle phase.

In certain embodiments, the PSA de-N-acetylase inhibitor compositions may be advantageously used in an anti-cancer therapy, particularly where the cancerous cells present a deNAc SA epitope on an extracellularly accessible cell surface (e.g., a deNAc SA epitope on an at least partially de-N-acetylated ganglioside or other glycoconjugate). In one embodiment, the cancer is one that presents a SEAM 3-reactive antigen. Cancers that present a SEAM 3-reactive antigen can be identified by methods known in the art. Exemplary methods of detection and diagnosis are described below.

Where the anti-cancer therapy comprises administration of a PSA de-N-acetylase inhibitor composition, the anti-cancer therapy can be particularly directed to dividing (replicating, proliferating) cancerous cells. As shown in the Examples below, PSA de-N-acetylase inhibitors were particularly effective against cancerous cells bearing the epitope specifically bound by SEAM 3 antibody. Also, the level of extracellularly accessible antigen bound by SEAM3 is increased during cell division as compared to non-dividing cells, and binding of SEAM3 drives the cell toward anaphase (into pre-$G_0$). Since most cancers are more rapidly dividing than normal cells of the same type, cells that possess a SEAM 3-reactive antigen are attractive for PSA de-N-acetylase inhibitor-based cancer therapy.

Thus the present disclosure particularly provides anti-cancer therapy directed toward cancerous cells involving administration of a PSA de-N-acetylase inhibitor having an epitope recognized by a SEAM 3 mAb. Cancers particularly amenable to PSA de-N-acetylase inhibitor therapy can be identified by examining markers of cellular proliferation (e.g., Ki-67 antigen) and/or by examining the presence/accessibility of the deNAc SA epitope bound by SEAM 3 in dividing cells (e.g., as in an in vitro assay).

Cancers having a cell surface-accessible deNAc SA epitope include those having an at least partially de-N-acetylated ganglioside and/or a protein having a sialic acid modification that contains a deNAc SA epitope. Cancers having de-N-acetylated gangliosides have been described.

The presence of de-N-acetyl sialic acid residues in normal human tissue appears to be transient and very low abundance, being found only in a few blood vessels, infiltrating mononuclear cells in the skin and colon, and at moderate levels in skin melanocytes. It is prevalent only in abnormal cells, such as melanomas, leukemias and lymphomas. Since expression of high levels of deNAc SA antigens (e.g., de-N-acetyl gangliosides) occurs predominantly in cancer cells, treatment with a PSA de-N-acetylase inhibitor can be used to induce cytotoxicity, and can block tumor growth. In addition, PSA de-N-acetylase inhibitor compositions can be used therapeutically to effect/prevent adhesion and invasion of cancer cells in other tissues.

Exemplary cancers presenting a deNAc SA epitope include cancer cells presenting a de-N-acetyl ganglioside containing a de-N-acetyl sialic acid residue (e.g. GM2alpha, GM1alpha, GD1beta, GM1b, GD1c, GD1alpha, GM3, GM2, GM1, GD13, GT13, GT1halpha, GD3, GD2, GD1b, GT1b, GQ1b, Gomega1halpha, GT3, GT2, GT1c, GQ1c, and GP1c). Of particular interest are gangliosides that contain two or more sialic acid residues linked by alpha 2-8 glycosidic bonds (e.g., GD1c, GT13, GD3, GD1b, GT1b, GQ1b, Gomega1halpha, GT3, GT1c, GQ1c, and GP1c) in which at least one residue is de-N-acetylated. In some embodiments, the ganglioside that contains two or more sialic acid residues linked by alpha 2-8 glycosidic bonds is a ganglioside other than GD3 and/or other than GM3. In some embodiments, the target of the cancer is a deNAc SA epitope other than one present on a de-N-acetylated ganglioside (e.g., a de-N-acetylated residue of a sialic acid-modified protein).

In one embodiment PSA de-N-acetylase inhibitors can be used to treat cancers that present a SEAM 3 reactive antigen on a cell surface, including cancers that exhibit an extracellularly accessible SEAM 3-reactive antigen during cell division.

It should be noted that while deNAc SA epitopes and/or SEAM 3-reactive antigens may be expressed at higher levels on a cancer cell compared to a non-cancerous cell, this is not a limitation of the therapies disclosed herein. For example, where the cancer involves a cell type that can be replenished (e.g., B cell, T cell, or other cell of hematopoietic origin, as in leukemias and lymphomas), inhibition of normal cell growth can be acceptable since damage to a subject by depleting such cells can be treated (e.g., with drugs to stimulate repopulation of normal cells, e.g., GM-CSF, EPO, and the like).

The methods relating to cancer contemplated herein include, for example, use of PSA de-N-acetylase inhibitor therapy alone or in combination with deNAc SA antigens as a anti-cancer vaccine or therapy, as well as use of antibodies generated using deNAc SA antigens in anti-cancer vaccines (e.g., by passive immunization) or therapies. The methods are useful in the context of treating or preventing a wide variety of cancers, including carcinomas, sarcomas, leukemias, and lymphomas.

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Further exemplary cancers that can be amenable to treatment using a methods disclosed herein include, but are not limited to, cancers of neuroectodermal and epithelial origin. Examples of cancers of neuroectodermal origin include, but are not limited to, Ewings sarcoma, spinal tumors, brain tumors, supratenbrial primitive neuroectodermal tumors of infancy, tubulocystic carcinoma, mucinous tubular and spindle cell carcinoma, renal tumors, mediastinum tumors, neurogliomas, neuroblastomas, and sarcomas in adolescents and young adults. Examples of epithelial origin include, but are not limited to, small cell lung cancer, cancers of the breast, eye lens, colon, pancreas, kidney, liver, ovary, and bronchial epithelium. In some embodiments, the subject methods do not include treatment of melanoma (i.e., the cancer is other than melanoma). In other embodiments, the subject methods do not include treatment of lymphoma (i.e., the cancer is other than lymphoma). In certain embodiments, the methods of the present disclosure are used to treat cancer cells known to express de-N-acetyl gangliosides include melanomas and some lymphomas. As noted above, cancers that overexpress the precursor gangliosides GM3 and GD3 are likely to also express the greatest amount of de-N-acetyl gangliosides on the cell surface, as thus express PSA de-N-acetylase.

Combinations with Other Cancer Therapies

Therapeutic administration of the subject PSA de-N-acetylase inhibitor compositions can include administration as a part of a therapeutic regimen that may or may not be in conjunction with additional standard anti-cancer therapeutics, including but not limited to immunotherapy, chemotherapeutic agents and surgery (e.g., as those described further below). In addition, therapeutic administration of the subject PSA de-N-acetylase inhibitor compositions can also be post-therapeutic treatment of the subject with an anti-cancer therapy, where the anti-cancer therapy can be, for example, surgery, radiation therapy, administration of chemotherapeutic agents, and the like. Use of monoclonal antibodies, particularly monoclonal antibodies that can provide for complement-mediated killing, and/or antibody-dependent cellular cytotoxicity-mediated killing, of a target cell are of particular interest (e.g., treatment with an anti-deNAc SA epitope antibody (e.g., SEAM 3) after identification of a primary tumor composed of cells expressing a deNAc SA epitope (e.g., a de-N-acetyl ganglioside)). Cancer therapy using a PSA de-N-acetylase inhibitor composition as disclosed herein in combination with immunotherapy that employs PSA antigen/anti-deNAc SA epitope antibodies is of particular interest, and is a specific exemplary embodiment of the present disclosure (U.S. Ser. No. 11/645,255 and PCT Application No. US2006/048850; incorporated herein by reference).

For example, the PSA de-N-acetylase inhibitor composition can be administered in combination with one or more chemotherapeutic agents (e.g., cyclophosphamide, doxorubicin, vincristine and prednisone (CHOP)), and/or in combination with radiation treatment and/or in combination with surgical intervention (e.g., pre- or post-surgery to remove a tumor). Where the PSA de-N-acetylase inhibitor is used in connection with surgical intervention, the PSA de-N-acetylase inhibitor can be administered prior to, at the time of, or after surgery to remove cancerous cells, and may be administered systemically or locally at the surgical site. The PSA de-N-acetylase inhibitor alone or in combinations described above can be administered systemically (e.g., by parenteral administration, e.g., by an intravenous route) or locally (e.g., at a local tumor site, e.g., by intratumoral administration (e.g., into a solid tumor, into an involved lymph node in a lymphoma or leukemia), administration into a blood vessel supplying a solid tumor, etc.).

Any of a wide variety of cancer therapies can be used in combination with the PSA de-N-acetylase inhibitor-based therapies described herein. Such cancer therapies include surgery (e.g., surgical removal of cancerous tissue), radiation therapy, bone marrow transplantation, chemotherapeutic treatment, biological response modifier treatment, and certain combinations of the foregoing.

Radiation therapy includes, but is not limited to, X-rays or gamma rays that are delivered from either an externally applied source such as a beam, or by implantation of small radioactive sources.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-1, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, epothilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and ZOLADEX®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL, TAXOTERE (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE☐ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In the treatment of some individuals with the compounds of the present disclosure, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. Rescue agents include those which do not interfere with the ability of the present inventive compounds to modulate cellular function.

Particular applications in which the subject methods and compositions find use include those described in U.S. Pat. Nos. 2,512,572; 3,892,801; 3,989,703; 4,057,548; 4,067,867; 4,079,056; 4,080,325; 4,136,101; 4,224,446; 4,306,064; 4,374,987; 4,421,913; 4,767,859; 3,981,983; 4,043,759; 4,093,607; 4,279,992; 4,376,767; 4,401,592; 4,489,065; 4,622,218; 4,625,014; 4,638,045; 4,671,958; 4,699,784; 4,785,080; 4,816,395; 4,886,780; 4,918,165; 4,925,662; 4,939,240; 4,983,586; 4,997,913; 5,024,998; 5,028,697; 5,030,719; 5,057,313; 5,059,413; 5,082,928; 5,106,950; 5,108,987; 4,106,488; 4,558,690; 4,662,359; 4,396,601; 4,497,796; 5,043,270; 5,166,149; 5,292,731; 5,354,753; 5,382,582; 5,698,556; 5,728,692; and 5,958,928; the disclosures of which are herein incorporated by reference.

Diagnostics

Antibodies reactive with a deNAc SA epitope can be used to detect deNAc SA antigens in a biological sample obtained from a subject having or suspected of having cancerous cells having a cell surface accessible deNAc SA epitope (e.g., a de-N-acetylated cell surface ganglioside) using anti-deNAc SA epitope antibodies in immunodiagnostic techniques as described in (See U.S. Ser. No. 11/645,255 and PCT Application No. US2006/048850; incorporated herein by reference). Such diagnostics can be useful to identify patients amenable to the therapies disclosed herein, and/or to monitor response to therapy.

Briefly, the antigen binding specificity of anti-deNAc SA epitope antibodies can be exploited in this context, to facilitate detection of deNAc SA epitopes on a cancerous cell in a sample with little or no detectable binding to host-derived PSA, thereby reducing the incidence of false positive results. Such detection methods can be used in the context of diagnosis, identification of subject suitable to PSA de-N-acetylase inhibitor-based therapy where the antibody specifically binds an deNAc SA epitope and/or a SEAM 3-reactive antigen, monitoring of therapy (e.g., to follow response to therapy), and the like.

Suitable immunodiagnostic techniques include, but are not necessarily limited to, both in vitro and in vivo (imaging) methods. Where the methods are in vitro, the biological sample can be any sample in which a deNAc SA antigen may be present, including but not limited to, blood samples (including whole blood, serum, etc.), tissues, whole cells (e.g., intact cells), and tissue or cell extracts. Assays can take a wide variety of forms, such as competition, direct reaction, or sandwich type assays. Exemplary assays include Western blots; agglutination tests; enzyme-labeled and mediated immunoassays, such as ELISAs; biotin/avidin type assays; radioimmunoassays; immunoelectrophoresis; immunoprecipitation, and the like. The reactions generally include detectable labels such as fluorescent, chemiluminescent, radioactive, enzymatic labels or dye molecules, or other methods for detecting the formation of a complex between antigen in the sample and the antibody or antibodies reacted therewith.

The assays can involve separation of unbound antibody in a liquid phase from a solid phase support to which antigen-antibody complexes are bound. Solid supports which can be used in the practice of the present disclosure include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Where a solid support is used, the solid support is usually first reacted with a solid phase component (e.g., an anti-deNAc SA epitope antibody) under suitable binding conditions such that the component is sufficiently immobilized to the support. Sometimes, immobilization to the support can be enhanced by first coupling the antibody to a protein with better binding properties, or that provides for immobilization of the antibody on the support with out significant loss of antibody binding activity or specificity. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind antibodies the support include polysaccharides, polylactic acids, polyglycolic acids, polymeric amino acids, amino acid copolymers, and the like, with the proviso that the molecule used to immobilize the antibody does not adversely impact the ability of the antibody to specifically bind antigen. Such molecules and methods of coupling these molecules to the antigens, are well known to those of ordinary skill in the art. See, e.g., Brinkley, M. A. Bioconjugate Chem. (1992) 3:2-13; Hashida et al., J. Appl. Biochem. (1984) 6:56-63; and Anjaneyulu and Staros, International J. of Peptide and Protein Res. (1987) 30:117-124.

After reacting the solid support with the solid phase component, any non-immobilized solid-phase components are removed from the support by washing, and the support-bound component is then contacted with a biological sample suspected of containing deNAc SA epitopes under suitable binding conditions. After washing to remove any non-bound ligand, a secondary binder moiety is added under suitable binding conditions, wherein the secondary binder is capable of associating selectively with the bound ligand. The presence or absence of the secondary binder can then be detected using techniques well known in the art.

An ELISA method can be used, wherein the wells of a microtiter plate are coated with anti-deNAc SA epitope antibody according to the present disclosure. A biological sample containing or suspected of containing a deNAc SA antigen (e.g., a tumor antigen having a deNAc SA epitope, such as a de-N-acetylated ganglioside), is then added to the coated wells. After a period of incubation sufficient to allow antibody binding, the plate(s) can be washed to remove unbound moieties and a detectably labeled secondary binding molecule added. The secondary binding molecule is allowed to react with any captured antigen, the plate washed and the presence or absence of the secondary binding molecule detected using methods well known in the art.

Where desired, the presence or absence of bound deNAc SA antigen from a biological sample can be readily detected using a secondary binder comprising an antibody directed against the antibody ligands. For example, a number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the antibodies and deNAc SA antigen form complexes under precipitating conditions. For example, the antibody can be attached to a solid phase particle (e.g., an agarose bead or the like) using coupling techniques known in the art, such as by direct chemical or indirect coupling. The antibody-coated particle is then contacted under suitable binding conditions with a biological sample suspected of containing deNAc SA antigen to provide for formation of particle-antibody-deNAc SA antigen complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

The test sample used in the diagnostics assays can be any sample in which a deNAc SA antigen may be present, including but not limited to, blood samples (including whole blood, serum, etc.), tissues, whole cells (e.g., intact cells), and tissue or cell extracts containing cells (e.g., tissue, isolated cells, etc.), a cell lysate (i.e., a sample containing non-intact cells), where each type of sample can contain elements of both types (e.g., a sample of cells can contain cell lysates, and vice versa). In some embodiments it may be desirable to conduct the assay using a sample from the subject to be diagnosed that contains intact, living cells. DeNAc SA antigen detection can then be assessed on an extracellular surface of the cells, and can further be assessed during cell division.

Diagnostic assays can also be conducted in situ. For example, anti-deNAc SA epitope antibodies can be detectably labeled, administered to a subject suspected of having a cancer characterized by cell surface expression of a deNAc SA epitope, and bound detectably labeled antibody detected using imaging methods available in the art.

The diagnostic assays described herein can be used to determine whether a subject has a cancer that is more or less amenable to therapy using a PSA de-N-acetylase inhibitor-based therapy, as well as monitor the progress of treatment in a subject. It also may be used to assess the course of other combination therapies (e.g., deNAc SA antigen vaccine and/or anti-deNAc SA antigen antibody therapy as described in (U.S. Ser. No. 11/645,255 and PCT Application No. US2006/048850; incorporated herein by reference). Thus, the diagnostic assays can inform selection of therapy and treatment regimen by a clinician.

Where the methods are in vitro, the biological sample can be any sample in which a SEAM 3-reactive antigen may be present, including but not limited to, blood samples (including whole blood, serum, etc.), tissues, whole cells (e.g., intact cells, i.e., cells that have not been subjected to permeabilization), or cell lysates (e.g., as obtained from treatment of a tissue sample). For example, the assay can involve detection of a SEAM 3-reactive antigen on cells in a histological tissue sample. For example, the tissue sample may be fixed (e.g., by formalin treatment) and may be provided embedded in a support (e.g., in paraffin) or frozen unfixed tissue.

The SEAM 3-reactive antigen can be detected by detection of specific binding of an antibody, usually a monoclonal antibody (mAb), that has the antigen-binding specificity of SEAM 3. In this embodiment, the SEAM 3-reactive antigen may be present on the cell surface at any stage of the cell cycle, including during cell division. Of note is that in some instances, cancers that present a SEAM 3-reactive antigen during cell division may present a lower or no detectable level of SEAM 3-reactive antigen when the cell is quiescent (i.e., not undergoing cell division). However, as illustrated in the examples below, SEAM 3-reactive antigen can be detected in non-dividing cells by detecting SEAM 3-reactive antigen in a permeabilized test cell. A test cancer cell that exhibits a pattern of staining with a SEAM 3 antibody (or an antibody having the antigen binding specificity of SEAM 3) that is distinct from a pattern of antibody staining in a normal cell is identified as a cancerous cell that exhibits a SEAM 3-reactive antigen. Such cancers are thus amenable to therapy with an antibody that specifically binds the SEAM 3-reactive antigen (e.g., the mAb SEAM 3).

The above-described assay reagents, including the antibodies generated by immunization with a deNAc SA antigen according to the methods described in U.S. Ser. No. 11/645,255 and PCT Application No. US2006/048850, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Kits & Systems

Also provided are kits and systems that find use in practicing the subject methods, as described above. For example, kits and systems for practicing the subject methods may include one or more pharmaceutical formulations that include a PSA de-N-acetylase inhibitor. As such, in certain embodiments the kits may include a single pharmaceutical composition present as one or more unit dosages. In yet other embodiments, the kits may include two or more separate pharmaceutical compositions.

Thus the kits can include one or more of, depending upon the intended use of the kit, the compositions described herein, such as: a PSA de-N-acetylase inhibitor, cells suitable related for assays or screening, an anti-deNAc SA epitope antibody, and the like. Other optional components of the kit include: buffers, etc., for administering a PSA de-N-acetylase inhibitor, and/or for performing a diagnostic assay. The various components of the kit may be present in separate containers or certain compatible components may be precombined into a single container, as desired.

In addition to the above components, the subject kits may further include instructions for practicing the subject methods. These instructions may be present in the kits in a variety of forms, one or more of which may be present in or on the kit. One form in which these instructions may be present is as printed information on a suitable medium or substrate, e.g., a piece or pieces of paper on which the information is printed, in or on the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

In a specific embodiment, a kit is provided for use in treating a host suffering from a cellular proliferative disease condition. This kit includes a pharmaceutical composition comprising an inhibitor of PSA de-N-acetylase, and instructions for the effective use of the pharmaceutical composition in a method of treating a host suffering from a cancerous condition by inhibiting the growth of a cancer cell in a subject. Such instructions may include not only the appropriate handling properties, dosing regiment and method of administration, and the like, but further include instructions to optionally screen the subject for a de-N-acetylated sialic acid (deNAc SA) epitope. This aspect can assist the practitioner of the kit in gauging the potential responsiveness of the subject to treatment with a PSA de-N-acetylase inhibitor, including timing and duration of treatment relative to the type and growth stage of the cancer. Thus in another embodiment, the kit may further include an antibody or other reagent for detecting a de-N-acetylated sialic acid (deNAc SA) epitope on an extracellularly accessible surface of a cancer cell, such as SEAM 3 (ATCC Deposit No. HB-12170). In another embodiment, the kit includes one or more PSA de-N-acetylase inhibitors that comprise a conjugate with a detectable label, such as a fluorophore.

The term "system" as employed herein refers to a collection of a PSA de-N-acetylase inhibitor and one or more second therapeutic agents, present in single or disparate compositions that are brought together for the purpose of practicing the subject methods. For example, separately obtained PSA de-N-acetylase inhibitor and chemotherapy dosage forms brought together and coadministered to a subject are an exemplary system according to the present disclosure.

The following examples further illustrate the present invention and should not be construed as in any way limiting its scope.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Synthesis of N-Acryl, N-Iodoacetyl and N-Propionyl Hexosamine Derivatives Using Acid Anhydrides Acrylic acid anhydride and iodoacetic anhydride were prepared by combining acrylic acid (0.47 ml, 7.0 mmol) or iodoacetic acid (1.30 g, 7.0 mmol) and dicyclohexylcarbodiimide (DCC, 0.66 g, 3.2 mmol) in chloroform (5 ml). The reaction was allowed to proceed for 10 minutes with occasional agitation, then filtered to remove the dicyclohexylurea by product. Propionic anhydride was obtained from Sigma-Aldrich (Saint Louis, Mo.).

Hexosamine hydrochloride salt, for example, mannosamine.HCl or galactosamine.HCl (0.5 g, 2.3 mmol; Sigma-Aldrich), was stirred in 10 ml of methanol. Sodium methoxide (4.6 ml of a 1M solution in methanol, 1 eq; Sigma-Aldrich) was added, and the hexosamine went into solution. Immediately afterwards, the acid anhydride was added to the hexosamine solution under a stream of argon with stirring. pH was maintained above 8 with sodium methoxide as determined by spotting on pH paper. After 20 minutes, two volumes of water were added and the reaction mixture was frozen and lyophilized. The extent of reaction was determined by thin layer chromatography (TLC) on aluminum-backed silica gel plates (EM Scientific obtained through ThermoFisher Scientific, Waltham, Mass.) developed with 2:1 $CHCl_3$:MeOH and stained with 1% ninhydrin (Sigma-Aldrich) in ethanol containing 5% acetic acid followed by heating on a hot plate.

Example 2

Synthesis of N-Acyl Hexosamine Derivatives Using Acyl Chlorides and N-Methanesulfonyl Hexosamine Derivatives Using Methanesulfonyl Chloride Hexosamine hydrochloride (0.5 g), for example, mannosamine.HCl or galactosamine.HCl (Sigma-Aldrich), was dissolved in 10 ml of $H_2O$. Five 60 µl aliquots of acyl chloride (~2 equivalents), for example, chloroacetyl chloride or methanesulfonyl chloride, were added while maintaining the pH between 8.5-9.0 with 2M NaOH. After adding the last aliquot and allowing completion of the reaction as indicated by no further change in pH, the pH was reduced to 7.0 with 2M HCl and the solvent removed by lyophilization.

All compounds were purified by resuspending the dry lyophilized residue in a small volume of 100% ethanol and stirring for 2 hours. Insoluble materials were removed by filtration and the product was obtained by partial evaporation of the ethanol under a stream of argon followed by adding water and lyophilization. The purity of the resulting products were confirmed by TLC as described previously and the structures confirmed by mass spectroscopy (Table 5) and NMR (Table 6).

TABLE 5

Mass Spectroscopy Data for Selected Hexosamine Derivatives
Summary of LC MS data for N-acyl hexosamine derivatives.

| Compound | Mode | Ion | Expected Mass | Observed Mass |
|---|---|---|---|---|
| ManNAcryl | Negative | [M − H]− | 232 | 232 |
|  |  | [M + Cl]− | 268 | 268 |
| ManNMeSul | Negative | [M − H]− | 256 | 256 |
|  |  | [M + Cl]− | 292 | 292 |
| ManNPr | Negative | [M − H]− | 234 | 234 |
|  |  | [M + Cl]− | 270 | 270 |
| GalNMeSul | Negative | [M − H]− | 256 | 256 |
|  |  | [M + Cl]− | 292 | 292 |
| GalNMeSul | Positive | [M + Na]+ | 280 | 280 |
|  |  | [M + K]+ | 296 | 296 |
| GalNlAc | Negative | [M − H]− | 346 | 346 |
|  |  | [M + Cl]− | 371 | 371 |
| Ac$_4$ManNAc | Positive | [M + H]+ | 390 | 390 |
|  |  | [M + Na]+ | 412 | 412 |
|  |  | [M − AcO]+ | 330 | 330 |
| Ac$_4$ManNAcryl | Positive | [M + H]+ | 402 | 402 |
|  |  | [M + Na]+ | 424 | 424 |
|  |  | [M − AcO]+ | 342 | 342 |
| Ac$_4$ManNMeSul | Positive | [M + Na]+ | 448 | 448 |
|  |  | [M − AcO]+ | 366 | 366 |

To estimate the purity of selected compounds, the integrated area under resonances in the 1H NMR spectra for the anomeric carbon proton was compared with that of protons in the N-acyl side chain that were well resolved. The NMR data is summarized in Table 6.

TABLE 6

NMR Data for Selected Hexosamine Derivatives
Summary of 1H NMR data for N-acyl hexosamine derivatives

| Compound | δ anomeric H | δ side chain H* | Ratio Expected | Ratio Observed |
|---|---|---|---|---|
| ManNMeSul | 5.018, 5.022; 5.255, 5.260 | 3.182, 3.154 | 1:3 | 1:3.38 |
| GalNMeSul | 4.617, 4.638; 5.293, 5.302 | 3.165, 3.172 | 1:3 | 1:3.21 |
| ManNPr | 5.037, 5.041; 5.121, 5.125 | 1.041, 1.060, 1.080, 1.1000, 1.107, 1.119, 1.126, 1.137, 1.145.1.156, 1.169.1.186, 1.205 | 1:5 | 1:9.19 |
| ManNAcryl | 5.075, 5.079; 5.166, 5.169 | 5.646, 5.651.5.671, 5.675; 5.794, 5.798, 5.820, 5.824, 5.832 | 1:2 | 1:1.70 |
| GalNAcryl | 4.694, 4.716; 5.273, 5.282 | 5.643, 5.648, 5.668, 5.673; 5.795, 5.799, 5.820, 5.823 | 1:2 | 1:2.05 |
| ManNClAc | 5.061, 5.065; 5.152, 5.155 | 4.186, 4.238 | 1:2 | 1:2.49 |
| ManNAc | 5.034, 5.038; 5.129, 5.133 | 2.058, 2.098 | 1:3 | 1:3.09 |

*Side chain resonances were selected based on chemical shifts that did not overlap with other resonances and could, therefore, be unambiguously identified and integrated.

Example 3

Synthesis of Peracetylated Hexosamine Derivatives

Peracetylated derivatives of N-acyl or N-methanesulfonyl hexosamines were prepared by the method of Luchansky et al (2003, Methods in Enzymology 362:249) modified as follows. Crude N-acyl or N-methanesulfonyl hexosamine prepared as described above (0.3 mmol) was solubilized in a small amount of DMSO, then diluted to 50 mM in pyridine (6 ml). A large excess of acetic anhydride (3 ml, 33 mmol) was added, the reaction was stirred overnight, then concentrated under vacuum. The dried residue was purified by chromatography on silica gel as described by Luchansky et al. The purity of the resulting product was analyzed by reverse-phase HPLC on a Waters Alliance HPLC (Milford, Mass.) using a Pharmacia Sephasil C18 (GE Healthcare Bio-Sciences Corp., Piscataway, N.J.) column (4.5 mm×250 mm) with a gradient of 5% to 40% acetonitrile in water.

Example 4

Synthesis of PSA Derivatives Containing PSA De-N-Acetylase Inhibitors

In addition to de novo biosynthesis of N-acetyl neuraminic acid from N-acetyl mannosamine, mammalian cells also have the capability of scavenging N-acetyl neuraminic acid from glycoconjugates and free sialic acid that are brought into the cell by endocytosis. The incorporation of inhibitors of PSA de-N-acetylase into PSA and PSA conjugates may be advantageous for targeting to cancer cells.

Colominic acid (100 mg, EY Scientific, San Mateo, Calif.) was suspended in 8 ml of water containing 10 mg of sodium borohydride (Sigma-Aldrich). Sodium hydroxide (1.8 ml of a 50% solution (ThermoFisher)) was added and the solution heated in a sealed reaction tube (Pierce Scientific, Rockford, Ill.) to between 90° and 100° C. in a heat block (Pierce) for 2 hours. After cooling to ambient temperature, the pH was adjusted to 8 using 2M HCl. The solution was dialyzed (Spectrapor 1 kDa cutoff, ThermoFisher) exhaustively in water and lyophilized. De-N-acetylated colominic acid (50 mg) was dissolved in water and the pH adjusted to 8 with 2M NaOH. Acyl chloride (10 equivalents based on a de-N-acetyl PSA residue mass of 250 g/mol of trichloroacetyl chloride, dichloroacetyl chloride, chloroacetyl chloride, or bromoacetyl chloride), or methanesulfonyl chloride, or acyl anhydride (acetic anhydride, propionic anhydride, iodoacetic anhydride or acryl anhydride) was added in 5 aliquots over several hours with stirring (all reagents were from Sigma-Aldrich). Acryl anhydride and iodoacetic anhydride were prepared as described in Example 1. The pH was maintained at 8-9 by adding 2M NaOH as required. After the acylation of de-N-acetyl colominic acid, the reaction mixture was dialyzed exhaustively in water and lyophilized.

Example 5

Synthesis of PSA Derivative Aggregate

PSA derivatives of Example 4 were treated with the exo-neuraminidase SiaA then heated at 50° C. for 1-2 hrs to form an aggregate of particles that were found to be readily taken up by cells. Specifically, the lyophilized re-N-acylated colominic acid powder (50 mg) was resuspended in 2.5 ml of 50 mM sodium phosphate buffer, pH 7. SIALIDASE A™ (10 µl, 1 U/ml, Prozyme) was added and the solution was transferred to dialysis tubing (1 kDa cutoff) then placed in 1 L of 50 mM sodium phosphate buffer, pH 7 at 37° C. for 3-4 days. N-acyl neuraminic acid released by the enzyme passes through the dialysis membrane but the enzyme and the polysialic acid terminating at the non-reducing end in a de-N-acetyl residue is retained.

After sialidase treatment, the product was diluted in water to <1 mg/ml and filtered to remove the enzyme (30 kDa cutoff membrane) and lyophilized. Prior to adding to cell culture, the lyophilized powder was resuspended in PBS buffer or cell culture media at a concentration of 2 mg/ml or greater up to 20 mg/ml and heated at 50° C. for 2 hrs to inactivate possible contaminating microorganisms and to facilitate the formation of aggregates. The aggregates of uniform size can be observed under a light microscope at a magnification of 40×.

Example 6

Synthesis of N-Substituted Neuraminic Acid Derivatives

PSA derivatives of Example 4 were converted to monomeric forms (N-substituted neuraminic acid derivatives) by standard acid hydrolysis or treatment with exoneuraminidase (sialidase) as follows. Degradation of polymeric derivatives to monomers using sialidases are performed as described above in Example 5 except that the reaction is performed in a smaller volume (10 ml) that is replaced at 24 hr intervals and is lyophilized. Alternatively, the polymeric derivatives are converted to monomers by acid hydrolysis in 20 mM sodium acetate buffer, pH 5.5 at 50° C. for 18 hrs.

Example 7

Cell Culture

Human melanoma SK-MEL 28, neuroblastoma CHP-134, and T-cell leukemia Jurkat cell lines were obtained from ATCC (Manassas, Va.). All cell lines were grown in RPMI 1640 media (UCSF Cell Culture Facility, San Francisco, Calif.), supplemented with 10% heat-inactivated fetal bovine serum (Gemini Bio-Products, West Sacramento, Calif.), non-essential amino acids, 100 units/ml penicillin/streptomycin, 110 µg/ml sodium pyruvate, and 2 mM glutamine (UCSF Cell Culture Facility). Jurkat cells were grown to a concentration of not more than $10^6$ cells/ml and adherent SK-MEL 28 and CHP-134 cells to a concentration of not more than $5 \times 10^4$ cells/cm$^2$.

Example 8

Expression of De-N-Acetyl PSA Antigens in Tumor Cell Lines

To determine whether tumor cell lines expressed PSA antigens that contained neuraminic acid (that is, de-N-acetyl neuraminic acid residues in PSA), binding of the monoclonal antibody SEAM 3 to CHP-134 neuroblastoma, Jurkat T-cell leukemia, and SK-MEL 28 melanoma cells was measured by flow cytometry. SEAM 3 specifically recognizes PSA containing neuraminic acid residues (U.S. Ser. No. 11/645,255 and PCT Application No. US2006/048850; incorporated herein by reference).

Cells (approximately $10^5$ per well) were plated onto a flat bottom 96-well tissue culture plate (Nunc) and incubated with growth medium overnight before assay. Cells were detached from the plate (Jurkat cells are non-adherent) by either trypsin (SK-MEL-28) or Cell Dispersal Reagent (CDR, Guava Technologies, Hayward, Calif.) (CHP-134) before being collected into a 96-round bottom plate (Falcon), spun at 1000×g for 5 minutes and fixed with ice-cold 1% (v/v) formaldehyde. After 20 minutes cells were pelleted by centrifugation (above) and incubated in a blocking solution of 3% (v/v) goat serum for 1 hour. After blocking, the primary antibodies were added and incubated overnight at 4° C. The cells were washed twice by pelleting and resuspension in ice-cold PBS. Secondary antibody (FITC-conjugated goat anti-mouse IgG (Fab)$_2$, Jackson Immunoresearch, West Grove, Pa.) was incubated with the cells for at least 1 hour at 4° C. in the dark. After another series of spins and washes (3 times) binding was analyzed by a Guava EastCyte flow cytometer (Guava Technologies). Control samples were treated with an isotype matched irrelevant antibody (Southern Biotech, Birmingham, Ala.), which were used to create baseline fluorescence, or positive control mAbs that are reactive with antigens specifically expressed by the cells (i.e. anti-GD3 mAb R24 (MEL-1 from Axxora LLC, San Diego, Calif.) for SK-MEL 28 cells.

As shown in FIG. 1, SEAM 3 binds to the surface of all three cell lines demonstrating that they all express PSA containing neuraminic acid on the cell surface.

Example 9

Incorporation of N-Modified Derivatives into PSA by Supplementing the Growth Media with N-Modified Hexosamine Derivatives Engineering sialic acid in cells is most often accomplished by supplementing the growth medium with mannosamine derivatives since such derivatives are direct precursors to the biosynthesis of N-acyl neuraminic acid and sialylated glyco-conjugates. However, metabolism of all hexosamine derivatives converges at N-acetyl glucosamine ("Essentials of Glycobiology" Ed. Varki et al, Cold Spring Harbor Press, NY 1999). Accordingly, it is possible that sialylated glycoconjugate substrates for PSA de-N-acetylase could also be derived from reservoirs of N-acyl glucosamine or N-acyl galactosamine.

To demonstrate that N-acyl galactosamine and N-acyl glucosamine derivatives can be incorporated into PSA, the growth media was supplemented with N-propionyl galactosamine and the cell surface expression of N-propionyl PSA was measured by flow cytometry using an antibody that is specific for N-propionyl PSA, SEAM 18 (Granoff et al. J. Immunol. 1998, 160:5028) as follows.

CHP-134, SK-MEL 28 and Jurkat cells were cultured in media containing N-propionyl galactosamine, N-propionyl mannosamine, or N-acetyl mannosamine (10 mM) or no supplement for 24 hours. To measure mAb binding, the cells were released from the plate, pelleted by centrifugation, washed with PBS, and fixed with 1% formaldehyde in PBS. All procedures were performed on ice. Cells were blocked with PBS containing 3% goat serum, then were incubated overnight at 4° C. with one of the following primary antibodies (~1 µg/ml), diluted in 3% goat serum: irrelevant isotype control mAbs IgG2a or IgG2b (Southern Biotech), SEAM 3 (Granoff et al. J. Immunol. 1998, 160:5028), or SEAM 18 (Granoff et al. J. Immunol. 1998, 160:5028). Cells were then washed and labeled with goat-anti-mouse FITC (1:1000, Jackson Immunoresearch, West Grove, Pa.). Fluorescence was measured on a Guava EasyCyte flow cytometer, using the Guava ExpressPlus assay (Guava Technologies) and the results are expressed as the percent of cells that are positive for mAb binding.

Figure 2:
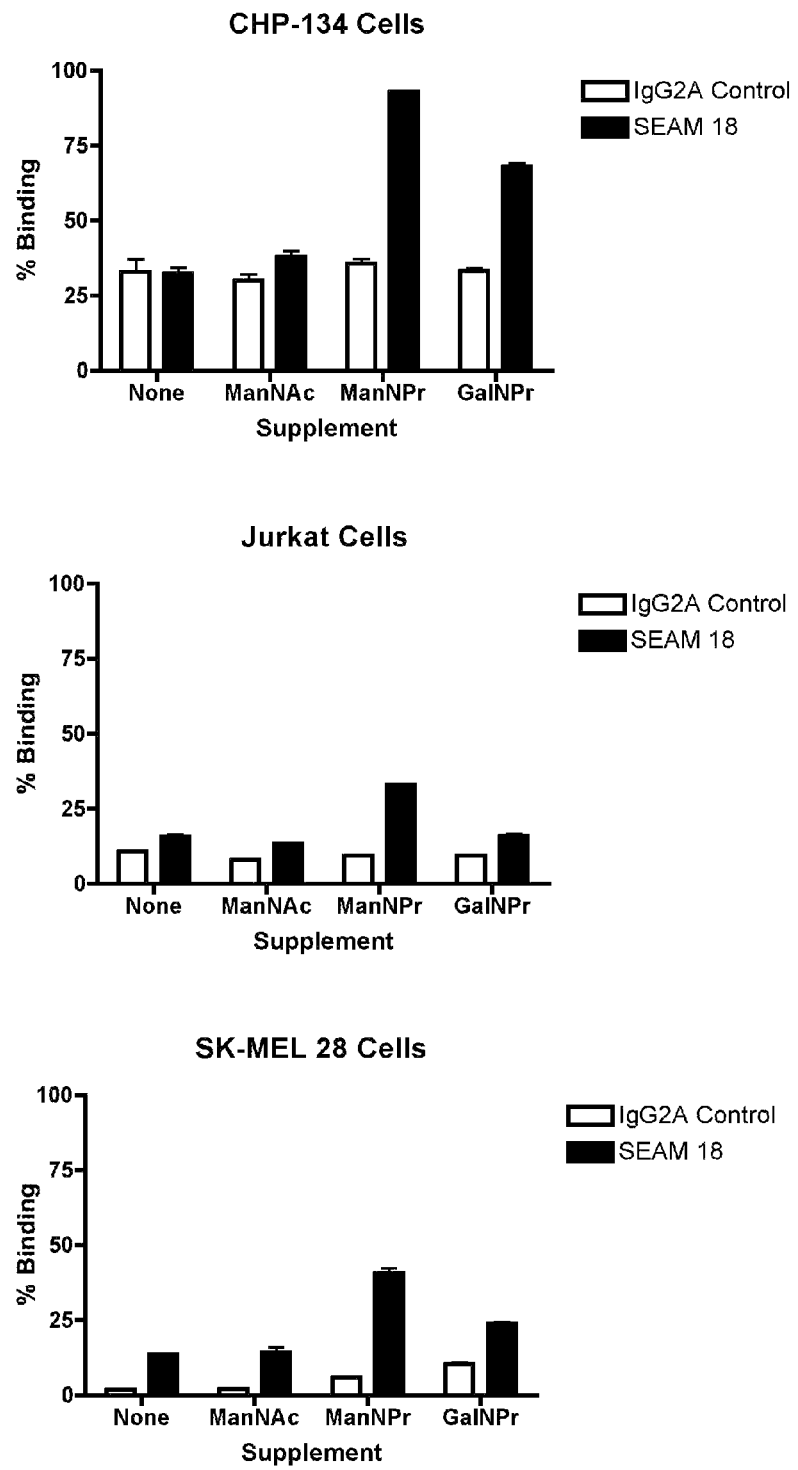
FIG. 2 is a graph showing that supplementing the culture media with either 10 mM N-propionyl mannosamine (ManNPr) or N-propionyl galactosamine (GalNPr) results in an increase in the expression of poly alpha (2→8) N-propionyl neuraminic acid glycoconjugates on the surface of CHP-134 neuroblastoma, Jurkat T-cell leukemia, and SK-MEL 28 melanoma cells as measured by an increase in binding by SEAM 18, a monoclonal antibody that specifically binds to poly alpha (2→8) N-propionyl neuraminic acid. The error bars represent the standard deviation of three replicate determinations.

As shown in FIG. 2, the percentage of cells for all three cell lines positive for SEAM 18 binding increases when the media is supplemented with N-propionyl mannosamine and N-propionyl galactosamine but not N-acetyl mannosamine. Binding by an isotype matched irrelevant control antibody was the same as that of SEAM 18 in the absence of a supplement or with N-acetyl mannosamine. The results show that surface expressed PSA derivatives can be derived from externally provided N-acyl galactosamine, N-acyl glucosamine or N-acyl mannosamine since the measured N-propionyl PSA produced with the N-propionyl galactosamine supplement could only have been derived from the conversion of N-propionyl galactosamine to N-propionyl glucosamine then to N-propionyl mannosamine.

Example 10

Effect of N-Acyl Hexosamine Derivatives on the Viability of Tumor Cells

The precursor for the biosynthesis of N-acetyl neuraminic acid in human cells is N-acetyl mannosamine. It has been shown that a wide variety of N-acyl groups can be incorporated into PSA in both cell culture and in living organisms by exogenously providing the desired N-acyl mannosamine derivative. Since PSA de-N-acetylase uses PSA as a substrate, the activity of the enzyme can be blocked by incorporating mechanism-based inhibitors into PSA by culturing cells in the presence of N-acyl mannosamine derivatives.

The effect of inhibitors of PSA de-N-acetylase on the viability of human tumor cell lines in culture was measured using a cell viability assay. Cells were incubated with N-acyl or methanesulfonyl hexosamine derivatives for 24 hours. Jurkat cells were incubated at a concentration of $2 \times 10^5$ cells/ml in round-bottom 96-well plates (Falcon), 200 µl/well. Adherent cells were incubated at a concentration of $1 \times 10^5$ cells/ml in flat-bottom 96-well plates (Nunc). Plates were then spun at 1,000×g for 5 minutes. SK-MEL 28 cells were release from the plate using a trypsin/EDTA solution (UCSF Cell Culture Facility). CHP-134 cells were released using CDR (Guava Technologies). All cells were resuspended in Guava ViaCount reagent and read on a Guava EasyCyte flow cytometer, using the Guava ViaCount assay (all from Guava Technologies).

Figure 3:
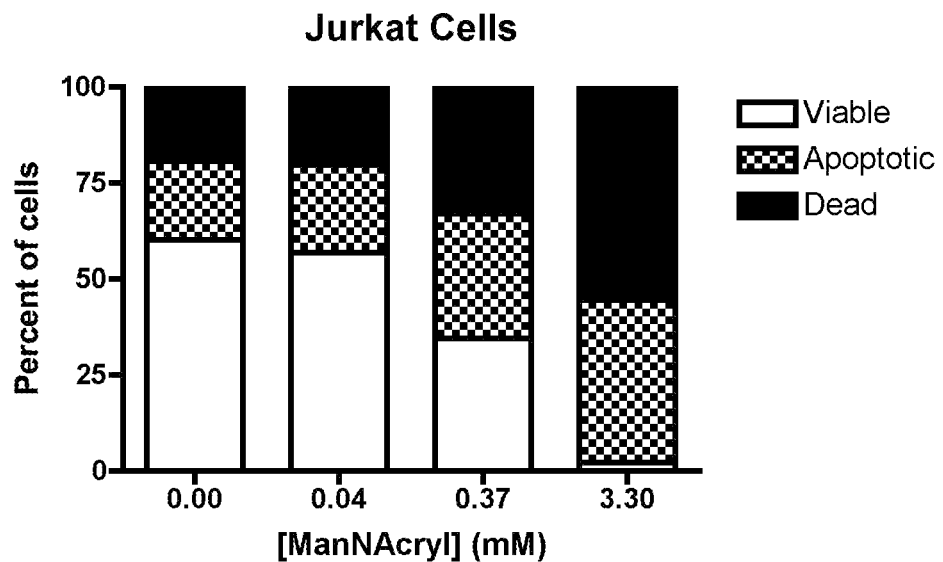
FIG. 3 is a graph showing the effect of four different concentrations of N-acryl mannosamine (ManNAcryl) in the cell culture media on viability, apoptosis, and death of Jurkat T-cell leukemia cells.
Figure 4:
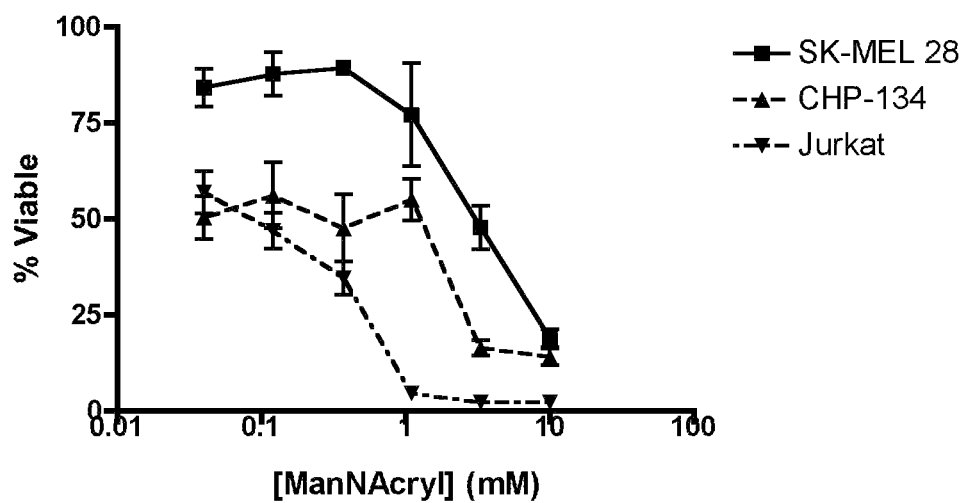
FIG. 4 is a graph comparing of the effect on viability of CHP-134 neuroblastoma, Jurkat T-cell leukemia, SK-MEL 28 melanoma cells on the concentration of N-acryl mannosamine (ManNAcryl) in the cell culture media. The error bars represent the standard deviation of three replicate determinations.

As shown in FIG. 3, N-acryl mannosamine taken up by the human T-cell leukemia cell line Jurkat reduces the viability of the cells by inducing apoptosis and cell death in a concentration-dependent manner. FIG. 4 shows the concentration-dependent effect of N-acryl mannosamine on reducing the cell viability of SK-MEL 28 melanoma, CHP-134 neuroblastoma, and Jurkat leukemia cells. The effect on the Jurkat cells is of particular interest because the cells do not have the ability to catabolize N-acyl mannosamine as a result of having an inactive N-acetyl glucosamine 2-epimerase gene (Luchansky et al J. Biol. Chem. 2003, 278:8035). As a result of the mutation, N-acyl mannosamine derivatives can only be used in biosynthesis of N-acyl neuraminic acid and will not affect catabolic enzymes such as hexosamine de-N-acetylases. The Jurkat cells are approximately 10-fold more sensitive to killing by the N-acryl mannosamine derivative than the other cell lines that are able to catabolize the derivative.

Figure 5:
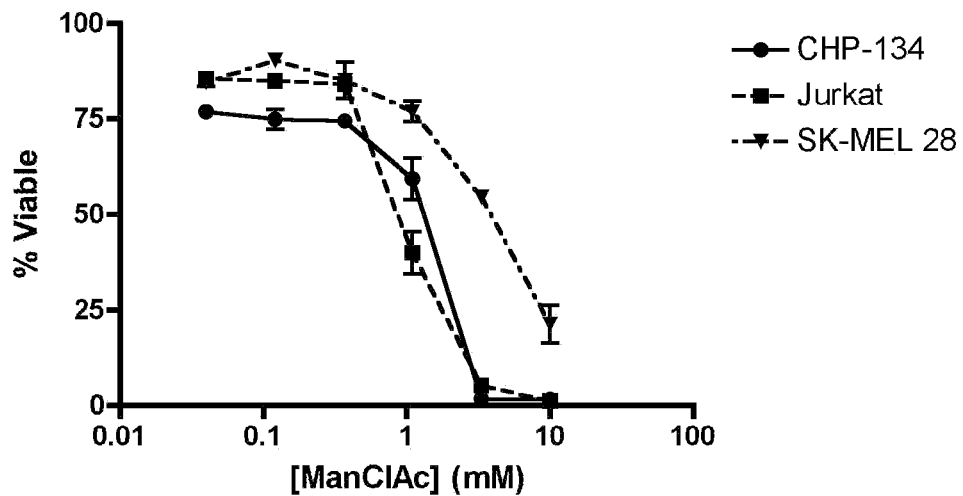
FIG. 5 is a graph comparing the effect on viability of CHP-134 neuroblastoma, Jurkat T-cell leukemia, SK-MEL 28 melanoma cells on the concentration of N-chloroacetyl mannosamine (ManNClAc) in the cell culture media. The error bars represent the standard deviation of three replicate determinations.

FIG. 5 shows the effect of N-chloroacetyl mannosamine (ManNClAc) concentration on the viability of CHP-134, Jurkat, and SK-MEL 28 cells after 24 hrs incubation with the inhibitor. The half-maximal decrease in viability occurs at a concentration of ManNClAc of approximately 1 mM for CHP-134 and Jurkat cells and approximately 8 mM for SK-MEL 28 cells.

Figure 6:
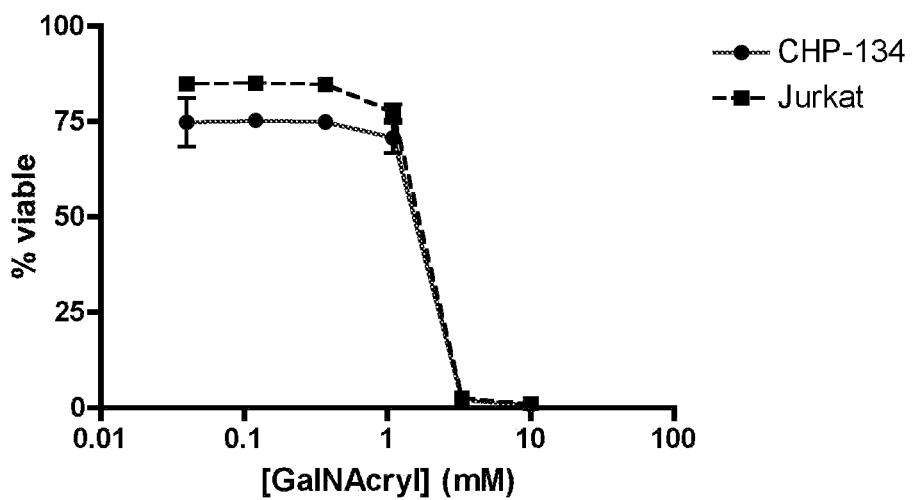
FIG. 6 is a graph comparing the effect on viability of CHP-134 neuroblastoma and Jurkat T-cell leukemia cells on the concentration of N-acryl galactosamine (GalNAcryl) in the cell culture media. The error bars represent the standard deviation of three replicate determinations.

FIG. 6 shows the concentration dependent effect of N-acryl galactosamine (GalNAcryl) on the viability of CHP-134 and Jurkat cells. Unlike ManNAcryl (FIG. 4), the concentration of GalNAcryl required for half-maximal reduction in viability is the same (3 mM) for both cell lines.

Figure 7:
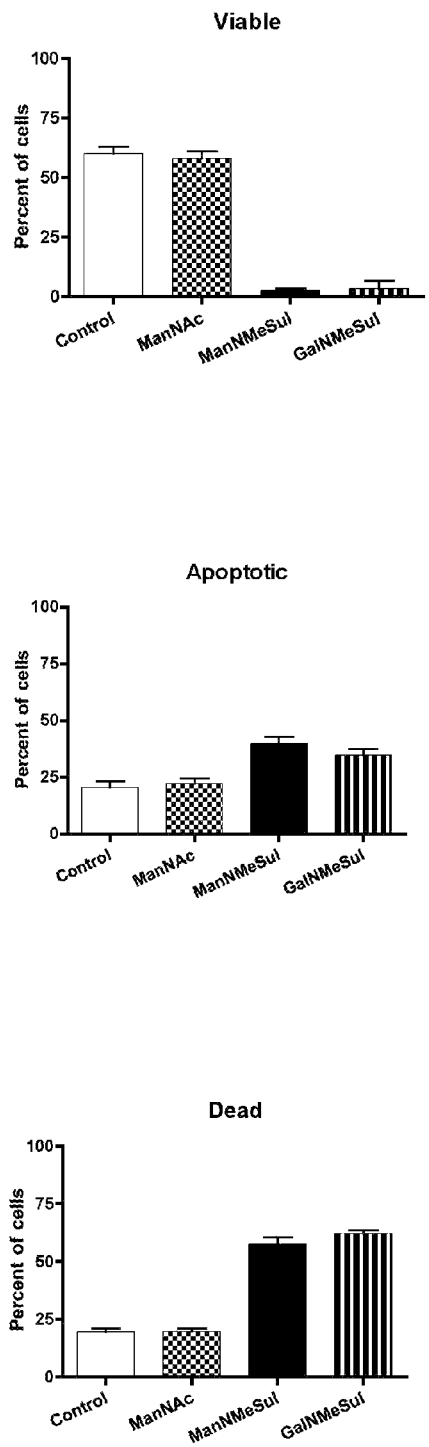
FIG. 7 is a graph comparing the effect of N-methanesulfonyl mannosamine (ManNMeSul) or N-methanesulfonyl galactosamine (GalNMeSul) at a concentration of 50 mM in the cell culture media on viability, apoptosis, and death of Jurkat T-cell leukemia cells. The error bars represent the standard deviation of three replicate determinations.
Figure 8:
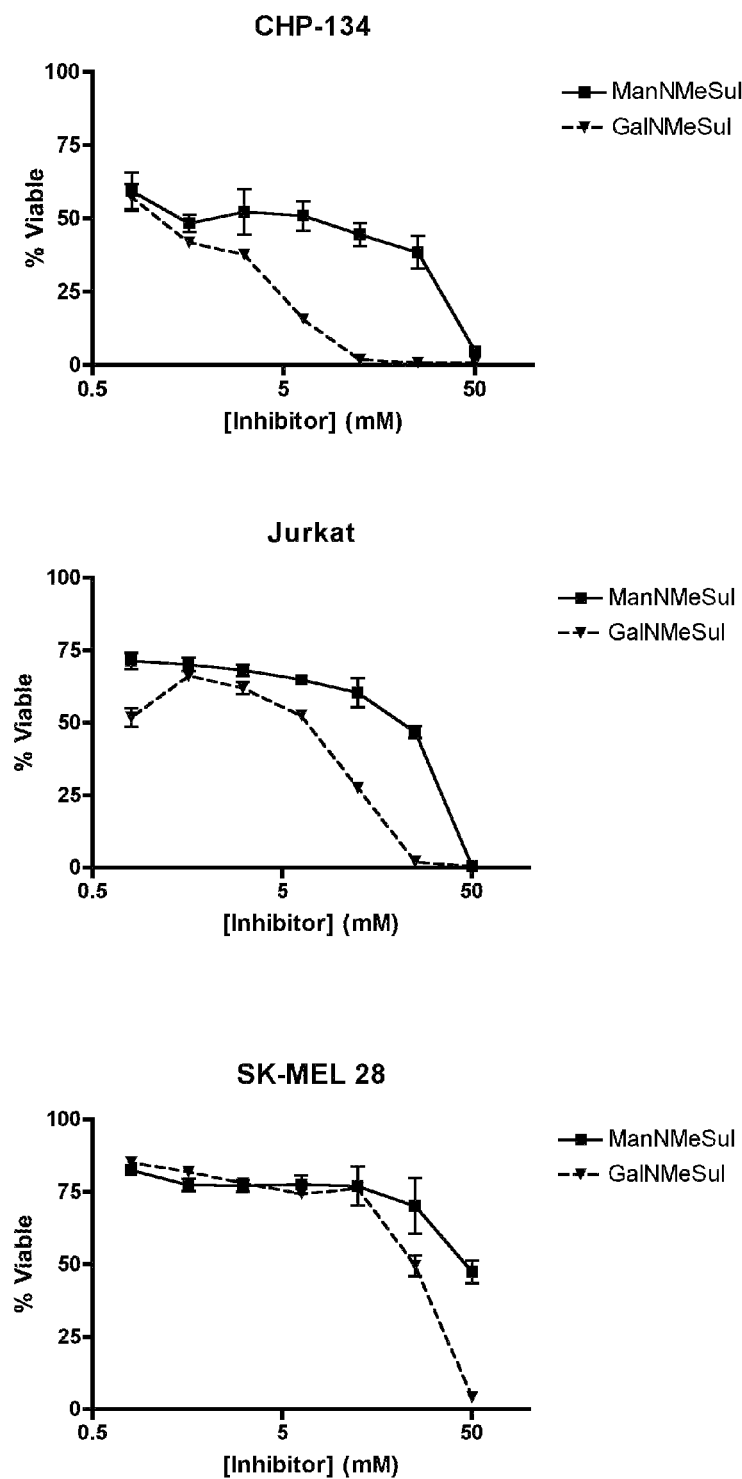
FIG. 8 is a graph comparing the effect on viability of CHP-134 neuroblastoma, Jurkat T-cell leukemia, SK-MEL 28 melanoma cells on the concentration of N-methanesulfonyl mannosamine (ManNMeSul) or N-methanesulfonyl galactosamine (GalNMeSul) in the cell culture media. The error bars represent the standard deviation of three replicate determinations.

FIG. 7 shows that biosynthetic incorporation of N-methanesulfonyl mannosamine (ManNMeSul) and N-methanesulfonyl galactosamine (GalNMeSul) can decrease cell viability by inducing apoptosis and cell death in Jurkat cells incubated for 24 hrs with either derivative at a concentration of 10 mM. FIG. 8 shows that cell viability of CHP-134, Jurkat and SK-MEL 28 cells is reduced with increasing concentrations of either inhibitor after 96 hrs incubation. Also, GalNMeSul appears to have an effect at lower concentrations than ManNMeSul. The N-methanesulfonyl derivatives, which are transition state inhibitors, are of particular interest. The N-methanesulfonyl group is approximately the same size as the normal N-acetyl group and, therefore, is unlikely to affect recognition of PSAs by receptors, and does not contain an inherently reactive functional group. Nevertheless, both N-methanesulfonyl mannosamine and N-methanesulfonyl galactosamine induce apoptosis in all three cell lines, thus demonstrating the effect of inhibiting PSA de-N-acetylase.

Example 11

Engineering PSA De-N-Acetylase Inhibitor Glycoconjugates by the Use of Chemically Synthesized PSA Derivatives Depending on the cell type, 15% to 90% of sialic acid expressed on surface glycoconjugates is obtained by scavenging or recycling from other glycoconjugates ("Essentials of Glycobiology" Ed. Varki et al, Cold Spring Harbor Press, NY 1999). Providing N-modified neuraminic acid derivative inhibitors of PSA de-N-acetylase as N-modified PSA or N-modified PSA glycoconjugates may be advantageous for the treatment of cancer since scavenging mechanisms bypass biosynthetic and catabolic pathways where N-modified hexosamine derivatives might be toxic to normal cells that express little or no PSA.

Figure 9:
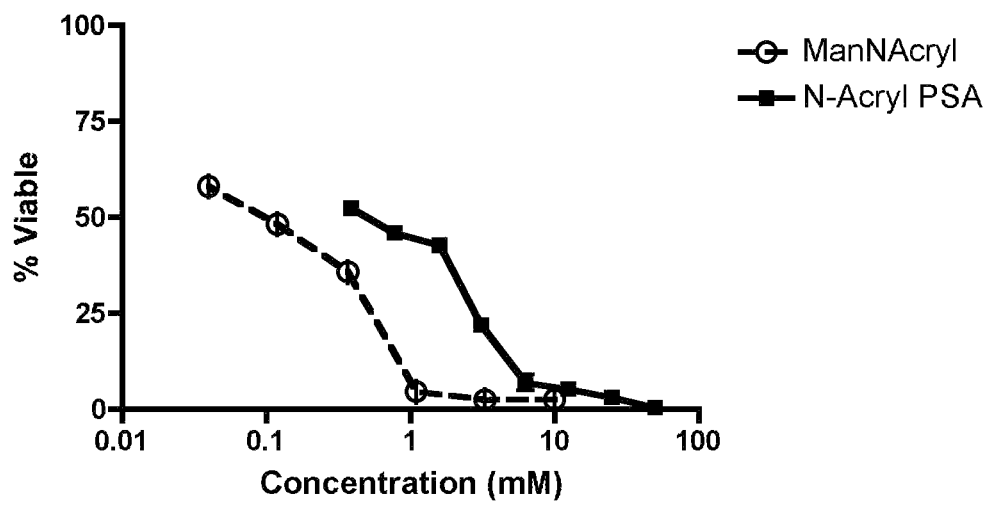
FIG. 9 is a graph comparing the effect of the concentration of poly alpha (2→8) N-acryl neuraminic acid in the cell culture media on the viability of Jurkat T-cell leukemia cells. The error bars represent the standard deviation of three replicate determinations.

Poly alpha (2→8) N-acryl neuraminic acid material produced according to Example 5 and sterile filtered to remove aggregate was added to the growth media, and its effect on cell viability in Jurkat cells compared to no supplement or N-acryl mannosamine was measured using the cell viability assay and the Guava EasyCyte flow cytometer as described above. The results are shown in FIG. 9. The N-acryl PSA reduced viability of the Jurkat cells after 24 hrs incubation. The results show that N-acryl PSA can be taken up by the cells and is cytotoxic. Although the concentration of N-acryl PSA required to induce cell death was higher for N-acryl PSA compared with N-acryl mannosamine, the use of N-acyl-modified PSA derivatives may be advantageous in treating cancer since they are less likely to be taken up by normal cells that express less sialic acid and little or no PSA.

What is claimed is:

1. A method of inhibiting growth of a cancerous cell in a subject, said method comprising:
    administering to the subject a pharmaceutical composition comprising an effective amount of an inhibitor of a polysialic acid (PSA) de-N-acetylase in a pharmaceutically acceptable vehicle, wherein the inhibitor is a monomer of an N-substituted derivative of a hexosamine compound of formula (I):

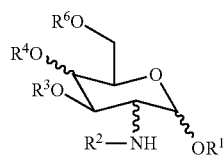

(I)

or the pharmaceutically acceptable salts, solvate, prodrug, anomers, tautomers and stereoisomers forms thereof;
    wherein $R^2$ is a radical selected from the group consisting of —C(O)CH$_2$F, —C(O)CH$_2$Cl, —C(O)CH$_2$Br, —C(O)CH$_2$I, and —C(O)CH=CH$_2$;
    each $R^1$, $R^3$, $R^4$ and $R^6$ is independently hydrogen or a substituted or unsubstituted moiety selected from the group consisting of heteroatom, cycloalkyl, heteroaryl, alkenyl, acetyl, sulfonyl, lipid, nucleic acid, peptide and polypeptide,
    with the proviso that said inhibitor of PSA de-N-acetylase is other than N-acryl glucosamine; an unacetylated or tetra-O-acetylated N-haloacetyl mannosamine; an unacetylated or tetra-O-acetylated N-haloacetyl galactosamine; and an unacetylated or tetra-O-acetylated N-haloacetyl glucosamine; and
    wherein said administering facilitates reduction in viability of cancerous cells exposed to said inhibitor.

2. The method of claim 1, wherein the cancer is a melanoma or a leukemia.

3. The method of claim 1, wherein the cancer is a neuroblastoma.

4. The method of claim 1 further comprising:
    administering at least one of an immunotherapy, a cancer chemotherapy or a radiation therapy to the subject.

5. The method of claim 1, wherein said hexosamine compound of formula (I) is selected from a mannosamine compound of formula (III), a galactosamine compound of formula (IV), or a glucosamine compound of formula (V):

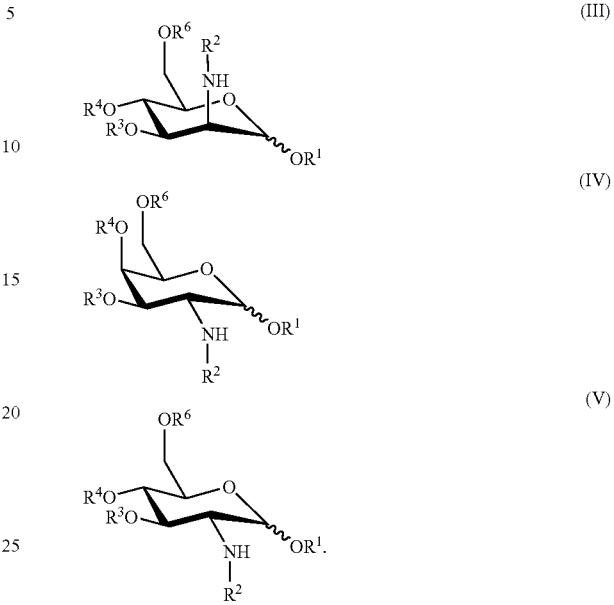

wherein each $R^1$, $R^3$, $R^4$ and $R^6$ is independently selected from the group consisting of hydrogen and acetyl and each $R^2$ is independently selected from a radical of the group consisting of —C(O)CH=CH$_2$, and —C(O)CH$_2$I.

6. The method of claim 1, wherein said inhibitor comprises an N-substituted hexosamine selected from the group consisting of: N-acryl mannosamine; N-acryl galactosamine; or the pharmaceutically acceptable salts, solvate, and prodrug forms thereof, anomers, tautomers and stereoisomers thereof, and derivatives thereof.

7. A pharmaceutical composition comprising an effective amount of inhibitor of a polysialic acid (PSA) de-N-acetylase in a pharmaceutically acceptable vehicle, wherein said inhibitor is a monomer of an N-substituted derivative of a hexosamine compound of formula (I):

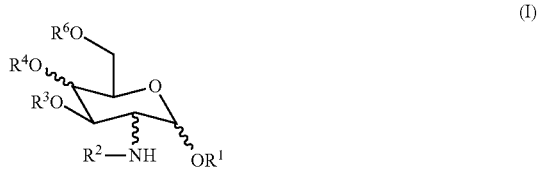

(I)

or the pharmaceutically acceptable salts, and prodrug forms thereof, anomers, tautomers and stereoisomers thereof;
    wherein $R^2$ is a radical selected from the group consisting of —C(O)CH$_2$F, —C(O)CH$_2$Cl, —C(O)CH$_2$Br, —C(O)CH$_2$I, and —C(O)CH=CH$_2$; and
    each $R^1$, $R^3$, $R^4$ and $R^6$ is independently hydrogen or a substituted or unsubstituted moiety selected from the group consisting of heteroatom, cycloalkyl, heteroaryl, alkenyl, acetyl, sulfonyl, lipid, nucleic acid, peptide and polypeptide,
    with the proviso that said inhibitor of PSA de-N-acetylase is other than N-acryl glucosamine; an unacetylated or tetra-O-acetylated N-haloacetyl mannosamine; an unacetylated or tetra-O-acetylated N-haloacetyl galactosamine; and an unacetylated or tetra-O-acetylated N-haloacetyl glucosamine.

8. The pharmaceutical composition of claim 7, wherein said hexosamine compound of formula (I) is selected from a mannosamine compound of formula (III), a galactosamine compound of formula (IV), or a glucosamine compound of formula (V):

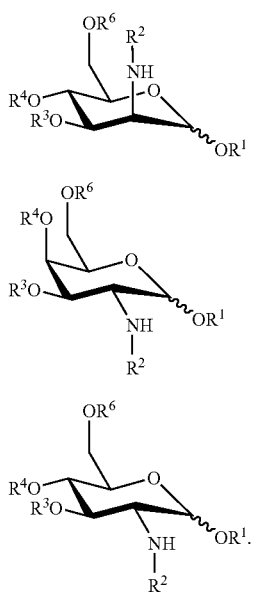

(III)

(IV)

(V)

wherein each $R^1$, $R^3$, $R^4$ and $R^6$ is independently selected from the group consisting of hydrogen and acetyl and each $R^2$ is independently selected from a radical of the group consisting of —C(O)CH=CH$_2$, and —C(O)CH$_2$I.

9. The pharmaceutical composition of claim 7, wherein said inhibitor comprises an N-substituted hexosamine selected from the group consisting of: N-acryl mannosamine; N-acryl galactosamine; or the pharmaceutically acceptable salts, and prodrug forms thereof, anomers, tautomers and stereoisomers thereof, and derivatives thereof.

10. A kit for use in treating a host suffering from a cellular proliferative disease condition, said kit comprising an effective amount of an inhibitor of polysialic acid (PSA) de-N-acetylase according to claim 7, and instructions for the effective use of said inhibitor in a method of inhibiting the growth of a cancerous cell.

11. The kit according to claim 10, wherein said kit further includes a diagnostic for detecting a de-N-acetylated sialic acid (deNAc SA) epitope.

12. The kit according to claim 11, wherein said diagnostic comprises an antibody or derivative thereof suitable for detecting a de-N-acetylated sialic acid (deNAc SA) epitope on an extracellularly accessible surface of a cancer cell.

13. The kit according to claim 11, wherein said antibody is SEAM 3 (ATCC Deposit No. HB-12170).

14. The pharmaceutical composition of claim 7, further comprising a pharmaceutically acceptable excipient.

15. The pharmaceutical composition of claim 14, wherein the pharmaceutically acceptable excipient is selected from the group consisting of mannitol, lactose, starch, magnesium stearate, sodium saccharin, talcum, cellulose, glucose, sucrose, magnesium carbonate, sodium acetate, sodium chloride, potassium chloride, calcium chloride and sodium lactate.

* * * * *